US 7,356,416 B2
Apr. 8, 2008

(12) United States Patent
Busa

(10) Patent No.: US 7,356,416 B2
(45) Date of Patent: Apr. 8, 2008

(54) METHOD AND SYSTEM FOR AUTOMATED INFERENCE CREATION OF PHYSICO-CHEMICAL INTERACTION KNOWLEDGE FROM DATABASES OF CO-OCCURRENCE DATA

(75) Inventor: William B. Busa, Renfrew, PA (US)

(73) Assignee: Cellomics, Inc., Pittsburgh, PA (US)

( * ) Notice: Subject to any disclaimer, the term of this patent is extended or adjusted under 35 U.S.C. 154(b) by 544 days.

(21) Appl. No.: 09/768,686

(22) Filed: Jan. 24, 2001

(65) Prior Publication Data

US 2002/0004792 A1 Jan. 10, 2002

Related U.S. Application Data

(60) Provisional application No. 60/201,105, filed on May 2, 2000, provisional application No. 60/177,964, filed on Jan. 25, 2000.

(51) Int. Cl.
*G01N 33/48* (2006.01)
*G06G 7/48* (2006.01)
*G06F 7/00* (2006.01)

(52) U.S. Cl. .................. 702/19; 702/20; 703/11; 707/1

(58) Field of Classification Search .................. 435/6; 702/19, 20
See application file for complete search history.

(56) References Cited

U.S. PATENT DOCUMENTS

| | | | |
|---|---|---|---|
| 4,942,526 A | 7/1990 | Okajima et al. | 364/419 |
| 5,021,220 A | 6/1991 | Mertens | 424/1.1 |
| 5,181,163 A | 1/1993 | Nakajima et al. | 364/419 |
| 5,218,695 A | 6/1993 | Noveck et al. | 395/600 |
| 5,235,522 A | 8/1993 | Bacus | 364/497 |
| 5,263,126 A | 11/1993 | Chang | 395/51 |
| 5,276,860 A | 1/1994 | Fortier et al. | 395/575 |
| 5,276,867 A | 1/1994 | Kenley et al. | 395/600 |
| 5,287,497 A | 2/1994 | Behera | 395/600 |
| 5,307,287 A | 4/1994 | Cramer, III et al. | 364/496 |
| 5,340,719 A | 8/1994 | Hajek et al. | 435/7.21 |
| 5,355,215 A | 10/1994 | Schrodeder et al. | 356/317 |
| 5,355,445 A | 10/1994 | Shibao et al. | 395/54 |
| 5,375,606 A | 12/1994 | Slezak et al. | 128/691 |
| 5,379,366 A | 1/1995 | Noyes | 395/54 |
| 5,406,480 A | 4/1995 | Kanno | 364/419 |
| 5,418,943 A | 5/1995 | Borgida et al. | 395/600 |
| 5,418,944 A | 5/1995 | DiPace et al. | 395/600 |
| 5,434,796 A | 7/1995 | Weininger | 364/496 |
| 5,443,791 A | 8/1995 | Cathcart et al. | 422/65 |
| 5,511,186 A | 4/1996 | Carhart et al. | 395/600 |
| 5,537,585 A | 7/1996 | Blickenstaff et al. | 395/600 |
| 5,548,061 A | 8/1996 | Masaki et al. | 530/324 |
| 5,554,505 A | 9/1996 | Hajek et al. | 435/721 |
| 5,615,112 A | 3/1997 | Liu Sheng et al. | 395/615 |
| 5,657,255 A | 8/1997 | Fink et al. | 364/578 |
| 5,670,113 A | 9/1997 | Akong et al. | 422/63 |
| 5,675,819 A | 10/1997 | Schuetze | 395/760 |
| 5,732,150 A | 3/1998 | Zhou et al. | 382/133 |
| 5,742,811 A | 4/1998 | Agrawal et al. | 395/606 |
| 5,751,605 A | 5/1998 | Hurst et al. | 364/496 |
| 5,806,060 A | 9/1998 | Borgida et al. | 707/3 |
| 5,808,918 A | 9/1998 | Fink et al. | 364/578 |
| 5,809,499 A | 9/1998 | Wong et al. | 707/6 |
| 5,819,266 A | 10/1998 | Agrawal et al. | 707/6 |
| 5,857,185 A | 1/1999 | Yamaura | 707/5 |
| 5,862,514 A | 1/1999 | Huse et al. | 702/22 |
| 5,867,118 A | 2/1999 | McCoy et al. | 342/90 |
| 5,873,080 A | 2/1999 | Coden et al. | 707/3 |
| 5,873,083 A | 2/1999 | Jones et al. | 707/4 |
| 5,892,838 A | 4/1999 | Brady | 382/115 |
| 5,901,069 A | 5/1999 | Agrafiotis et al. | 364/528.03 |

(Continued)

FOREIGN PATENT DOCUMENTS

EP 0367544 A2 10/1989

(Continued)

OTHER PUBLICATIONS

W. Salmonsen, K.Y.C. Mok, P. Kolatkar, S. Subbiah, "BioJAKE: A Tool for the Creation, Visualization and Manipulation of Metabolic Pathways," Bioinformatics Centre, Jan. 1999, pp. 392-400.

(Continued)

*Primary Examiner*—Shubo (Joe) Zhou
(74) *Attorney, Agent, or Firm*—Workman Nydegger

(57) ABSTRACT

Methods and system for automated inference of physico-chemical interaction knowledge from databases of term co-occurrence data. The co-occurrence data includes co-occurrences between chemical or biological molecules or co-occurrences between chemical or biological molecules and biological processes. Likelihood statistics are determined and applied to decide if co-occurrence data reflecting physico-chemical interactions is non-trivial. A next node or an unknown target representing chemical or biological molecules in a biological pathway is selected based on co-occurrence values. The method and system may be used to further facilitate a user's understanding of biological functions, such as cell functions, to design experiments more intelligently and to analyze experimental results more thoroughly. Specifically, the present invention may help drug discovery scientists select better targets for pharmaceutical intervention in the hope of curing diseases. The method and system may also help facilitate the abstraction of knowledge from information for biological experimental data and provide new bioinformatic techniques.

6 Claims, 10 Drawing Sheets

U.S. PATENT DOCUMENTS

| | | | |
|---|---|---|---|
| 5,914,891 A | 6/1999 | McAdams et al. | 364/578 |
| 5,930,154 A | 7/1999 | Thalhammer-Reyero | 364/578 |
| 5,940,817 A | 8/1999 | Kishi et al. | 706/46 |
| 5,950,192 A | 9/1999 | Moore et al. | 707/3 |
| 5,965,352 A | 10/1999 | Stoughton et al. | 435/4 |
| 5,966,712 A | 10/1999 | Sabatini et al. | 707/104 |
| 5,970,482 A | 10/1999 | Pham et al. | 706/16 |
| 5,970,500 A | 10/1999 | Sabatini et al. | 707/104 |
| 5,977,890 A | 11/1999 | Rigoutsos | 341/55 |
| 5,978,804 A | 11/1999 | Dietzman | 707/10 |
| 5,980,096 A | 11/1999 | Thalhammer-Reyero | 364/578 |
| 5,989,835 A | 11/1999 | Dunlay et al. | 435/7.2 |
| 6,023,659 A | 2/2000 | Seilhamer et al. | 702/19 |
| 6,073,138 A | 6/2000 | de I'Etraz et al. | 707/104 |
| 6,081,620 A | 6/2000 | Anderholm | 382/194 |
| 6,094,652 A | 7/2000 | Faisal | 707/5 |
| 6,103,479 A | 8/2000 | Taylor | 435/7.2 |

FOREIGN PATENT DOCUMENTS

| | | |
|---|---|---|
| EP | 0811421 A1 | 6/1997 |
| WO | WO91/06050 A1 | 10/1990 |
| WO | WO96/22575 A1 | 1/1996 |
| WO | WO97/42253 A1 | 5/1997 |
| WO | WO98/38490 A1 | 2/1998 |
| WO | WO98/15825 | 4/1998 |
| WO | WO98 43182 | 10/1998 |
| WO | WO99/05323 | 2/1999 |
| WO | WO00/15847 | 3/2000 |

OTHER PUBLICATIONS

W. Fujibuchi, K. Sato, H. Ogata, S. Goto, M. Kanehisa, "KEGG and DBGET/LinkDB: Integration of Biological Relationships in Divergent Molecular Biology Data," Institute for Chemical Research, Kyoto University, 1998, pp. 35-40.

P.D. Karp, "Database Links are a Foundation for Interoperability," Aug. 1996, pp. 273-279, TibTech, (vol. 14).

Paley, P.D. Karp, "Adapting EcoCyc for Use on the World Wide Web," Gene 172 (1996) GC43-GC50, Mar. 28, 1996, pp. 43-50.

P.D. Karp, "Computer Corner-Metabolic Databases," Mar. 23, 1998, pp. 114-116, TIBS.

C. Allee, "Data Management for Automated Drug Discovery Laboratories," XP-002134398, Aug. 21, 1996, pp. 307-310.

A.R. Kerlavage, W. FitzHugh, A. Glodek, J. Kelley, J. Scott, R. Shirley, G. Sutton, Man Wai-Chiu, O. White, M.D. Adams, "Data Management and Analysis for High-Throughput DNA Sequencing Projects," IEEE Engineering in Medicine and Biology, Nov./Dec. 1995, pp. 710-717.

K.A. Giuliano, D. Lansing Taylor, "Flourescent-Protein Biosensors: New Tools for Drug Discovery," Mar. 1998, pp. 135-140, TibTech (vol. 16).

Cellomics Vital Knowledge, Smarter Screening and Lead Optimization with Cellomics™ High content Screening Systems and Informatics Tools In An Integrated Drug Discovery Solution. 1999.

K.A. Giuliano, R.L. DeBiasio, R. T.Dunlay, A. Gough, J.M. Volosky, J. Zock, G.N. Pavlakis, D. Lansing Taylor, "High-Content Screening: A New Approach to Easing Key Bottlenecks in the Drug Discovery Process," Journal of Biomolecular Screening, 1997, pp. 249-259, (vol. 2, No. 4) Winter.

B.R. Conway, L.K. Minor, J.Z. Xu, J.W. Gunnet, R. DeBiasio, M.R. D'Andrea, R. Rubin, R. DeBiasio, K. Giuliano, L. Zhou, K.T. Demarest, "Quantification of G-aprotein Couples Receptor Internalization Using G-Protein Coupled Receptor-Green Flourescent Protein Conjugates with the ArrayScan™ High-Content Screening Flourescent Protein Conjugates with the ArrayScan™ High-Content Screening System," Journal of Biomolecular Screening, 1999, pp. 75-86, (vol. , No. 2), April.

Ethan B. Arutunian, Deirdre R. Meldrum, Neal A. Friedman and Stephen E. Moody, "Flexible Software Architecture for User-Interface and Machine Control in Laboratory Automation," BioTechniques 25:698-705 (Oct. 1998).

Blaschke et al., "Automatic Extraction Of Biological Information From Scientific Text: Protein-Protein Interactions", ISBM'99, pp. 60-67.

Chen et al., "Automatic Construction Of Networks Of Concepts Characterizing Document Databases", IEEE Transactions On Systems, Man, And Cybernetics, vol. 22, No. 5, Sep./Oct. 1992, pp. 885-902.

Chen et al., "An Algorithmic Approach to Concept Exploration In A Large Knowledge Network (Automatic Thesaurus Consultation): Symbolic Branch-And-Bound Search vs. Connectionist Hopfield Net Activation", Journal Of The American Society For Information Science, 36(5), 1995, pp. 348-369.

Craven et al., "Constructing Biological Knowledge Bases By Extracting Information From Text Sources", ISBM'99, pp. 77-86.

Gordon et al., "Toward Discovery Support Systems: A Replication, Re-Examination, And Extension Of Swanson's Work On Literature-Based Discovery Of A Connection Between Raynaud's And Fish Oil", Journal Of The American Society For Information Science, 47(2), 1996, pp. 116-128.

Swanson et al., "An Interactive System For Finding Complementary Literatures: A Stimulus To Scientific Discovery", Artificial Intelligence 91 (1997), pp. 183-203.

Karp Peter D., "Pathway Databases: A Case Study in Computational Symbolic Theories," Computers and Science, vol. 293, Sep. 14, 2001, pp. 2040-2044.

Gifford, David K., "Blazing Pathways Through Genetic Mountains," Computers and Science, vol. 293, Sep. 14, 2001, pp. 2049-2051.

Overbeek et al., "Representation of Function: The Next Step", Pub. On-line Jan. 31, 1997, www.mcs.anl.gov/compbio/publications/function_pap.html, pp. 1-13.

Rip et al., "Co-word maps of biotechnology: an example of cognitive scientometrics," SCIENTOMETRICS, vol. 6, No. 6, 1984, pp. 381-400.

Church K. W. et al., "Word Association Norms, Mutual Information, and Lexicography," Computational Linguistics, Cambridge, MA, vol. 16, No. 1, Mar. 1990.

Wayne C. Guida, "Software For Structure-Based Drug Design", Current Opinion in Structural Biology, 1994, 4: 777-781.

"Bioinformatics, Pharmaceutical Informatics And Drug Discovery", www.basefour.com/what_is.html, pp. 1-3, 2000.

Commercial Bioinformatics Software, www.uk.embnet.org/data/www/CCP11/commercial_software.txt.html, pp. 1-12, 2000.

Hwa A. Lim, "Bioinformatics And Cheminformatics In The Drug Discovery Cycle", in:Lecture Notes In Computer Science #1278, 1997, pp. 30-43.

Nathan Goodman, "The Fundamental Principles For Constructing A Successful Biological Laboratory Informatics System", pp. 1-11, 1996.

Rebecca N. Lawrence, "Enhancing Information Sharing", DDT vol. 4, No. 11, Nov. 1999, pp. 494-495.

Matthew Thorne, "InfoTech Pharma '98: Managing The Knowledge", DDT vol. 3, No. 5, May 1998, pp. 197-199.

Quinn et al., "Development Of Internet-Based Multimedia Applications", TiBS 24, Aug. 1999, pp. 1-4.

Watt et al., "Approaches To Higher-Throughput Pharmacokinetics (HTPK) In Drug Discovery", DDT vol. 5, No. 1, Jan. 2000, pp. 17-24.

Craw et al., "Automated Knowledge Refinement For Rule-Based Formulations Expert System", PSTT vol. 2, No. 9, Sep. 1999, pp. 383-385.

Steven Bottomley, "Bioinformatics—Value added Databases", DDT, vol. 4, No. 1, Jan. 1999, pp. 42-44, DDT. vol. 4, No. 10, Oct. 1999, pp. 482-484.

Andrade et al., "Bioinformatics: From Genome Data To Biological Knowledge", Current Opinion In Biotechnology 1997, 8, pp. 675-683.

Profiles Monitor, various articles, DDT, vol. 3, No. 11, Nov. 1998, pp. 525-527.

Monitor, various articles, DDT vol. 3, No. 9, Sep. 1998, pp. 426-428.

Peter Murray-Rust, "Bioinformatics And Drug Discovery", Current Opinion in Biotechnology, 1994, 5:648-653.

Karp et al., "Representation of Metabolic Knowledge: Pathways", Artificial Intelligence Center, ISMB-94, pp. 203-211, 1994.

Ogata et al., "KEGG: Kyoto Encyclopedia of Genes And Genomes", Institute for Chemical Research, Nucleic Acids Research, 1999, vol. 27, No. 1, pp. 29-34.

Heidtke et al., "BioSim—A New Qualitative Simulation Environment For Molecular Biology", Max-Planck-Institute For Molecular Genetics, ISMB-98, pp. 85-94, 1998.

Igarashi et al., "Development Of A Cell Signaling Networks Database", Division of Chem-Bio Informations, National Institute Of Health Sciences, 1997, pp. 187-197.

Goto et al., "Organizing And Computing Metabolic Pathway Data In Terms Of Binary Relations", Institute For Chemical Research, Kyoto University, 1997, pp. 175-186.

Kraus et al., Systems Analysis In Cell Biology: From The Phenomenological Description Towards A Computer Model Of The Intracellular Signal Transduction Network, Experientia 49 (1993) Birkhäuser Verlag, Ch-4010 Basel/Switzerland, pp. 245-257.

Ogata et al., "Computation With The KEGG Pathway Database", Institute For Chemical Research, Kyoto University, BioSystems 47 (1998), pp. 119-128.

Karp et al., "EcoCyc: Encyclopedia Of *Escherichia coli* Genes And Metabolism", Nucleic Acids Research, 1998, vol. 26, No. 1, pp. 50-53.

Bono et al., "Reconstruction Of Amino Acid Biosynthesis Pathways From The Complete Genome Sequence", Institute For Chemical Research, Kyoto University, 1998 by Cold Spring Harbor Laboratory Press ISSN 1054-9803/98, pp. 203-210.

Goto et al., "LIGAND Database For Enzymes, Compounds And Reactions", Institute For Chemical Research and Graduate School Of Agricultures Sciences, Kyoto University, 1999 Oxford University Press, Nucleic Acids Research, vol. 27, No. 1, pp. 377-379.

Goto et al., "LIGAND: Chemical Database For Enzyme Reactions", Institute For Chemical Research and Graduate School Of Agricultural Sciences, Kyoto University, Oxford University Press, Bioinformatics, vol. 14, No. 7, 1998, pp. 591-599.

Ermolaeva et al., "Data Management And Analysis For Gene Expression Arrays", Nature Genetics, vol. 20, Sep. 1998, pp. 19-23.

McGregor et al., "Pharmacophore Fingerprinting. I. Application To QSAR And Focused Library Design", Affymax Research Institute, J. Chem. Inf. Comput. Sci. 1999, 39, pp. 569-574.

Collins et al., "Driving Drug Discovery And Patient Therapy Via The Encapsulation And Fusion Of Knowledge", Momentum Healthcare Ltd, Pharmaceutical Sciences Research Institute, Drug Design And Discovery, 1999, vol. 16, pp. 181-194.

Mark Collins, "Empiricism Strikes Back: Neural Networks In Biotechnology", Bio/Technology, vol. 11, Feb. 1993, pp. 163-166.

Hopfinger et al., "Extraction Of Pharmacophore Information From High-Throughput Screens", Current Opinion In Biotechnology, 2000, 11, pp. 97-103.

Peter A. Hunt, "QSAR Using 2D Descriptors And TRIPOS' SIMCA", NRC Terlings Park, Journal Of Computer-Aided Molecular Design, 1999, 13, pp. 453-467.

Schmalhofer et al., "Cooperative Knowledge Evolution: A Construction-Integration Approach To Knowledge Discovery In Medicine", German Research Center For Artificial Intelligence, Methods Of Information In Medicine, 1998, 37, pp. 491-500.

Mars et al., "Knowledge Acquisition And Verification Tools For Medical Expert Systems", Med Decis Making, 1987, 7, pp. 6-11.

Robinson et al., "Self-Organizing Molecular Field Analysis: A Tool For Structure-Activity Studies", Physical And Theoretical Chemistry Laboratory, Oxford University, J. Med. Chem., 1999, 42, pp. 573-583.

Sung et al., "Evolutionary Optimization in Quantitative Structure-Activity Relationship: An Application Of Genetic Neural Networks", Department of Chemistry, Harvard University, J. Med. Chem., 1996, 39, pp. 1521-1530.

Hans Matter, "Selecting Optimally Diverse Compounds From Structure Databases: A Validation Study Of Two-Dimensional And Three-Dimensional Molecular Descriptors", J. Med. Chem., 1997, 40, pp. 1219-1229.

A. David Rodrigues, "Preclinical Drug Metabolism In The Age Of High-Throughput Screening: An Industrial Perspective", Pharmaceutical Research, vol. 14, No. 11, 1997, pp. 1504-1510.

Gorse et al., "Molecular Diversity And Its Analysis", DDT vol. 4, No. 6, Jun. 1999, pp. 257-264.

Cramer et al., "Prospective Identification Of Biologically Active Structures By Topomer Shape Similarity Searching", Tripos, Inc. and Bristol-Myers Squibb, J. Med. Chem., 1999, 42, pp. 3919-3933.

Manallack et al., "Neural Networks In Drug Discovery: Have They Lived Up To Their Promise?", Eur. J. Med. Chem., 34, 1999, pp. 195-208.

The Knowledge Access Suite—Much More Then Just Data Mining, www.datamining.com/ka-suite.htm (various other articles attached all accessed at dataming.com), 2000.

Data Mining: An Introduction: Clementine-Working With Health Care, www.spss.com/cool/papers/clem_healthcare1.htm (other various downloads from this site), 2000.

Cognos Scenario, www.cognos.com/scenario/index.html, 1998.

Discover New Drugs, Discover Synt:em, www.syntem.com, 1999.

"DIVA Desktop Decision Support For Life Sciences Research For Windows 95, Windows 98, Windows NT", Oxford Molecular, 1999, pp. 1-4.

Oxford Molecular—Solutions For Discovery Research, www.oxmol.com/software/diamond/background.shtml (various other articles from this site), 1999.

MDL Information Systems, Inc., www.mdli.com/cgi/dynamic/product.html?uid=$uid&key=$key&id=40 (various other articles from this site), 2000.

Tripos, Inc. Discovery Research, www.tripos.com/research/typapp.html. (various other articles from this site), 1999.

"Bionumerik Pharmaceuticals", Red Herring Magazine, www.rhventure.mag/issue67/news-feature-du99-bionum.html, pp. 1-2, 1999.

"Chemistry And Biological Sciences", Silicon Graphics, Inc. (SGI), 2000, www.sgi.com/chembio/cust_success/bionumerik.html, pp. 1-2.

"CS 267 Assignment One—Drug Design", garnet.berkeley.edu/~abeand/cs267/assignment1.html, pp. 1-2, 2000.

"Cray And BioNumerick Pharmaceuticals: Engineering More Rapid Cures For Today's Diseases", www.cray.com/features/bionumerik.html, pp. 1-3, 2000.

"BioNumerik Reports Preclinical Antitumor Data On Two Novel Supercomputer Engineered Anticancer Agents At 89th Annual AACR Conference", www.prostatecancer.com/otherinfo/story2-aacs.html-ssi, pp. 1-3, 1998.

"Agile Business Rule Processing", The Haley Enterprise, Inc., 1999, pp. 1-9.

"Knowledge Management And Knowledge Automation Systems", Gallagher Financial System, Inc., pp. 1-6, 1999.

Various pages from www.haley.com/4013219860515857/0000025120WhitePapers.html, etc, 2000.

Arbour Group, Software Specialists To The Pharmaceutical And Medical Device Industries, www.arbourgroup.com, (various other articles from this site), 2000.

Nanodesign—Partners In Drug Discover, EMD Facts-Evolutionary Molecular Design, www.nanodesign.com/EMD_facts.htm, (various other articles from this site), 2000.

BIOREASON—Automated Reasoning Systems For Drug Discovery, www.bioreason.com, (various other articles from this site), 2000.

Next Generation Software Tools For Early Drug Development, www.innaphase.com/pub/products.htm, (various other articles from this site), 2000.

LION Bioscience—Genomics, Informatics, Solutions, ww.lion-ag.de, (various other articles from this site), 2000.

Inpharmatica—World-Class Bioinformatics, www.inpharmatics.co.uk, (various other articles from this site), 2000.

"Project Explorer: Enabling Knowledge-Led R& D Projects", Synomics, www.synomocs.com/m/products/projectexplorer.htm, pp. 1-3, 2000.

PharMatrix—Providing Information, Knowledge & Project Management Solutions For Pharmaceutical Discovery & Development, www.base4.com, (various other articles from this site), 2000.

Rowe et al., "Artificial Intelligence In Pharmaceutical Product Formulation: Neural Computing And Emerging Technologies", PSTT vol. 1, No. 5, Aug. 1998, pp. 200-205.

Rowe et al., "Artificial Intelligence In Pharmaceutical product Formulation: Knowledge-Based And Expert Systems", PSTT vol. 1, No. 4, Jul. 1998, pp. 153-159.

FIG. 3

```
AU - MARTINEZ R
AU - EDWARDS CA
TI - EXPRESSION, PURIFICATION
     AND FUNCTIONAL
     CHARACTERIZATION OF THE
     DNA-BINDING DOMAIN OF THE
     HERPES SIMPLEX VIRUS TYPE 1
     UL9 PROTEIN.
RN - EC 3.4.21.5 (THROMBIN)
RN - 0 (VIRAL PROTEINS)
RN - 115004-77-8- (HERPES SIMPLEX
     VIRUS TYPE 1 PROTEIN UL9)
RN - 9007-49-2 (DNA)
```
⟵ 68, 70

```
THROMBIN
VIRAL PROTEINS
HERPES SIMPLEX VIRUS TYPE 1
     PROTEIN UL9
DNA
```
⟵ 72

```
FILTER WORDS:
VIRAL PROTEINS
```
⟵ 74

```
THROMBIN
HERPES SIMPLEX VIRUS TYPE 1
     PROTEIN UL9
DNA
```
⟵ 76

| INFERENCE DATABASE | | CO-OCCURRENCE COUNTS | | |
|---|---|---|---|---|
| ID | NAME | ID1 | ID2 | COUNT |
| 1 | THROMBIN | 1 | 2 | 12 |
| 2 | HERPES SIMPLEX... | 1 | 3 | 4 |
| 3 | DNA | 2 | 3 | 44 |

⟵ 78

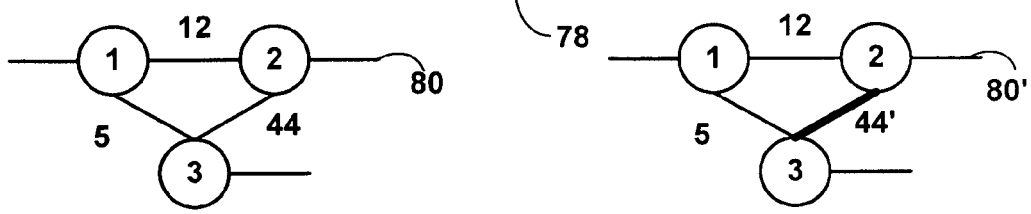

INFERENCE: HERPES SIMPLEX VIRUS TYPE 1 PROTEIN UL9 INTERACTS WITH DNA ⟵ 82

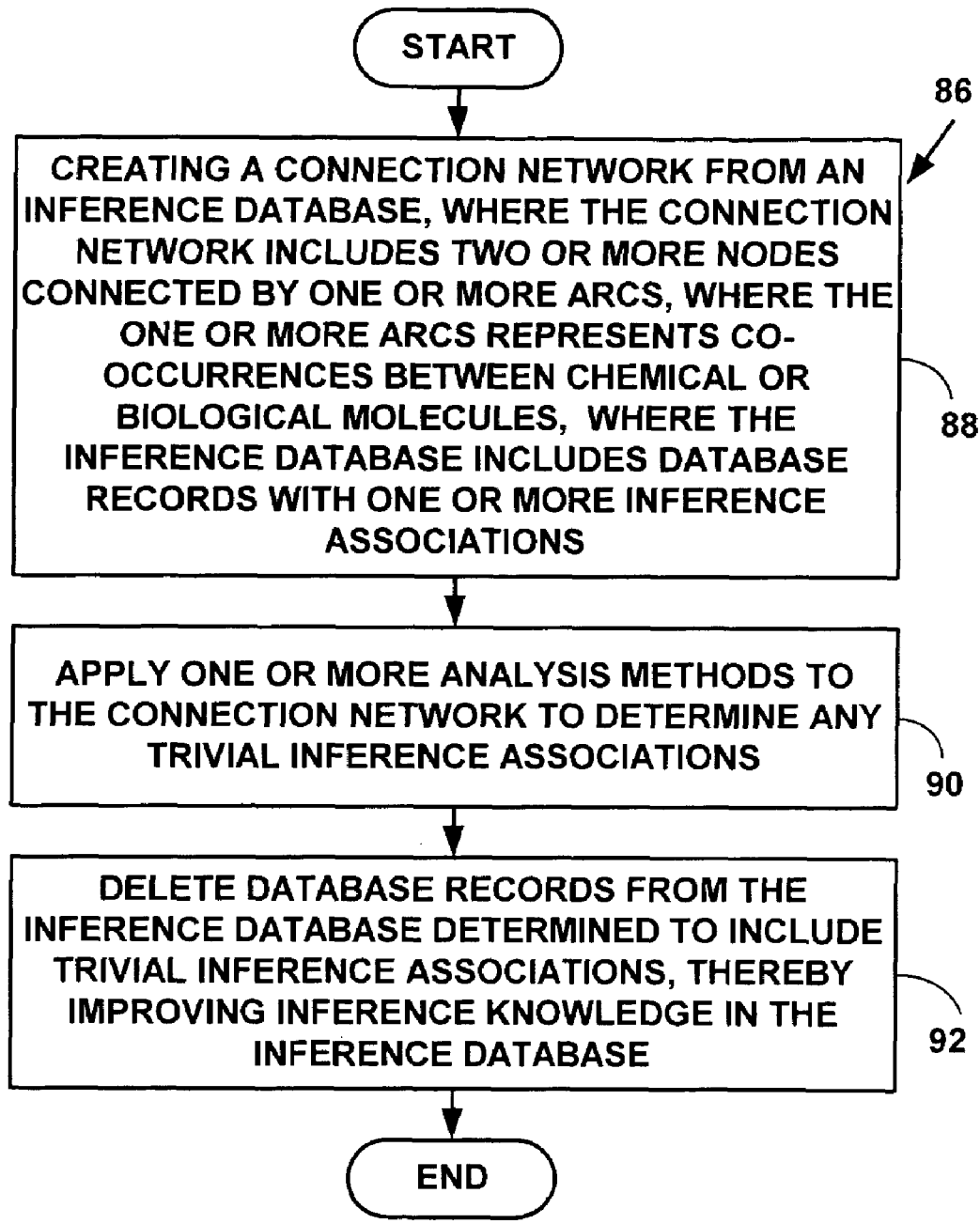

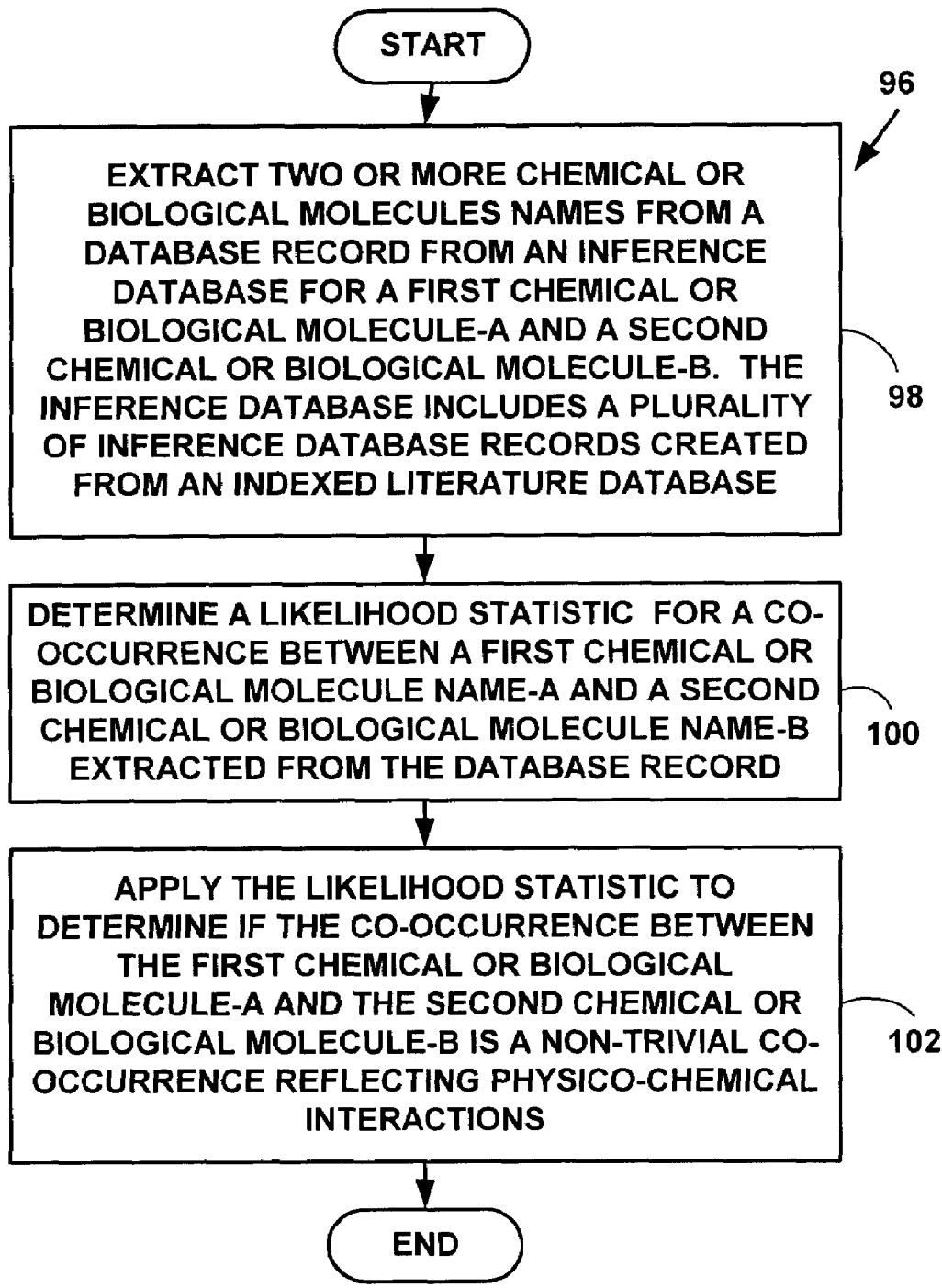

METHOD AND SYSTEM FOR AUTOMATED INFERENCE CREATION OF PHYSICO-CHEMICAL INTERACTION KNOWLEDGE FROM DATABASES OF CO-OCCURRENCE DATA

CROSS REFERENCES TO RELATED APPLICATIONS

This application claims priority from U.S. Provisional Application Nos. 60/177,964, filed on Jan. 25, 2000, and 60/201,105 filed on May 2, 2000.

FIELD OF THE INVENTION

This invention relates to analyzing experimental information. More specifically, it relates to a method and system for automated inference creation of physico-chemical interaction knowledge from databases of co-occurrence data.

BACKGROUND OF THE INVENTION

Traditionally, cell biology research has largely been a manual, labor intensive activity. With the advent of tools that can automate much cell biology experimentation (see for example, U.S. patent application Ser. Nos. 5,989,835 and 6,103,479), the rate at which complex information is generated about the functioning of cells has increased dramatically. As a result, cell biology is not only an academic discipline, but also the new frontier for large-scale drug discovery.

Cells are the basic units of life and integrate information from Deoxyribonucleic Acid ("DNA"), Ribonucleic Acid ("RNA"), proteins, metabolites, ions and other cellular components. New compounds that may look promising at a nucleotide level may be toxic at a cellular level. Florescence-based reagents can be applied to cells to determine ion concentrations, membrane potentials, enzyme activities, gene expression, as well as the presence of metabolites, proteins, lipids, carbohydrates, and other cellular components.

Innovations in automated screening systems for biological and other research are capable of generating enormous amounts of data. The massive volumes of data being generated by these systems and the effective management and use of information from the data has created a number of very challenging problems.

To fully exploit the potential of data from high-volume data generating screening instrumentation, there is a need for new informatic and bioinformatic tools. As is known in the art, "bioinformatic" techniques are used to address problems related to the collection, processing, storage, retrieval and analysis of biological information including cellular information. Bioinformatics is defined as the systematic development and application of information technologies and data processing techniques for collecting, analyzing and displaying data obtained by experiments, modeling, database searching, and instrumentation to make observations about biological processes.

Recent advances in the automation of molecular and cellular biology research including High Content and High Throughput Screening ("HCS" and "HTS," respectively), automated genome sequencing, gene expression profiling via complementary DNA ("cDNA") microarray and biochip technologies, and protein expression profiling via mass spectrometry and others are producing unprecedented quantities of data regarding the chemical constituents (i.e., proteins, nucleic acids, and small molecules) of cells relevant to health and disease.

There are several problems associated with analyzing chemical constituent data generated by automated screening systems. One problem is that there is a major bottleneck in the analysis and application of such data. Tasks such as pharmaceutical research typically require knowledgeable experts (i.e., molecular and cellular biologists) to place such data within a "biological context." For example, given a gene expression profile indicating that expression of Gene X is inhibited in cells treated with Compound Y, this datum becomes significant for the drug discovery process only upon inspection by a cell biologist who is able to reason: "I know that the protein coded for by Gene X affects Protein Z, the over-activity of which underlies disease A. Therefore, these data indicate that Compound Y may prove useful as a drug for the treatment of disease A." Such reasoning is also called an "inference."

Such reasoning requires detailed knowledge of the sequences of physico-chemical interactions between molecules in cells (i.e., the cell biologist must know that the protein encoded by Gene X affects Protein Z). Such "manual" assessment of data's significance is becoming more and more unworkable as the rate of data production continues to increase.

Another problem is that analysis of biological data in light of molecular interactions is not easy to automate. Given a suitable electronic database of known physico-chemical interactions between molecules in cells, much of this manual inspection and reasoning could be automated, increasing the efficiency of tasks such as drug discovery and genetic analysis. However as currently practiced in the art, constructing such a database would be an "expert systems engineering" task, requiring domain experts to enter into the database their explicit and implicit knowledge regarding known interactions between biological molecules.

As is known in the art, an "expert system" is an application program that makes decisions or solves problems in a particular field, such as biology or medicine, by using knowledge and analytical rules defined by experts in the field. An expert system typically uses two components, a knowledge base and an inference engine, to automatically form conclusions. Additional tools include user interfaces and explanation facilities, which enable the system to justify or explain its conclusions. "Manual expert system engineering" includes manually applying knowledge and analytical rules defined by experts in the field to form conclusions or inferences. Typically, such conclusions are then manually added to a knowledge base for a particular field (e.g., biology).

In the human genome alone there are approximately 100,000 genes, encoding a like number of proteins (i.e., each of which may occur in several distinct forms due to splice variants and covalent modifications). In addition there are a large but unknown number (e.g., thousands to tens of thousands) of different small organic molecules whose interactions with each other and with proteins and nucleic acids should also be represented in a comprehensive physico-chemical interaction database. It is very difficult to determine with any degree of certainty the total number of such interactions, or even the number of currently known interactions. However the combinatorial problem presented by numbers of this magnitude prevents development of truly comprehensive and up-to-date biomolecule interaction databases when their construction is approached as an expert system engineering task based on direct input of knowledge by experts. As is known in the art, a "combinatorial problem" is a problem related to probability and statistics, involving the study of counting, grouping, and arrangement of finite sets of elements.

There have been attempts to create databases including biomolecule interactions with inferences via the manual "expert systems engineering" approach. However, such expert systems currently elect to severely restrict the scope of their coverage (e.g., to a few tens or hundreds of "key" proteins, or to the biomolecules of only the simplest organisms, such as bacteria and fungi, whose relatively small genomes encode many fewer proteins than does the human genome). In addition such manual expert systems typically make little, if any, effort to incorporate new information in a timely fashion.

Such expert system engineering approaches include, for example: (1) Pangea Systems Inc.'s (1999 Harrison Street, Suite 1100, Oakland, Calif. 94612) "EcoCyc database." Information on this database and the other databases can be found on the Internet. This database's coverage in general includes basic metabolic pathways of the 10 bacterium, E. coli; (2) Proteome Inc.'s (100 Cummings Center, Suite 435M, Beverly, Mass. 01915) "Bioknowledge Library" This is a suite of databases of curated information including in general sequenced genes of the yeast, S. cerevisiae, and the worm, C. elegans. A number of well-established protein-protein interactions are included; and (3) American Association for the Advancement of Science's (1200 New 15 York Ave. NW, Washington, D.C. 20005) "Science's Signal Transduction Knowledge Environment". This connections map database seeks to document some of the best-established biomolecular interactions in a select number of signal transduction pathways.

However, such selected databases and others known in the art, take a manual "expert system engineering" approach or semi-automated approaches to populating the databases (e.g., human authorities manually input into a database their individual understandings of the details of what is known regarding individual biomolecular interactions.)

Some of these problems have been overcome in co-pending application Ser. No. 09/769,169, entitled "Method and system for automated inference of physico-chemical interaction knowledge via co-occurrence analysis of indexed literature databases," assigned to the same Assignee as the present application.

However, it is also highly desirable to automatically construct logical associations from the inferences created via co-occurrence analysis of indexed literature databases, to represent a temporal sequence of physico-chemical interactions actually used by living cells to regulate or to achieve a biological response. In molecular cell biology, such a temporal sequence of physico-chemical interactions is called a biological or cell "pathway."

There have been attempts to collect and store data associated with biological pathways. Such attempts include for example, "Ecocyc" from Pangea (see, e.g., Nucleic Acids Research 26:50-53 (1998), Ismb 2:203-211 (1994)); "KEGG" pathway database from Institute for Chemical Research, Kyoto University (see, e.g., Nucleic Acids Research 27:377-379 (1999), Nucleic Acids Research 27:29-34 (1999)); "CSNDB" links to from Japanese National Institute of Health Sciences (see, e.g., Pac Symp. Biocomput 187-197 (1997)); "SPAD" from Graduate School of Genetic Resources Technology, Kyushu University, Japan; "PUMA" now called "WIT" from Computational Biology in the Mathematics and Computer Science Division at Argonne National Laboratory; and others. However, such pathway databases typically do not use automated co-occurrence analysis of indexed literature databases to represent a temporal sequence of physico-chemical interactions.

Thus, it is desirable to automatically determine temporal sequences of physico-chemical interactions with co-occurrence analysis of indexed literature databases that can be used to determine biological pathways. Such an approach should help permit the construction of comprehensive databases of knowledge concerning temporal sequences of physico-chemical interactions to determine biological pathways.

SUMMARY OF THE INVENTION

In accordance with preferred embodiments of the present invention, some of the problems associated with analyzing co-occurrence data are overcome. A method and system for automated inference of physico-chemical interaction knowledge from databases of term co-occurrence data is presented.

One aspect of the invention includes a method for measuring a strength of co-occurrence data. Co-occurrence data include counts of co-occurrences between two or more chemical or biological molecule names in documents such as scientific publications, or counts of co-occurrences between one or more chemical or biological molecule names and one or more terms describing or naming biological processes (for example, "cell division", "apoptosis", or "terminal differentiation"). The method includes determining a Likelihood statistic and applying it to the co-occurrence to determine if a co-occurrence reflecting physico-chemical interactions is non-trivial.

Another aspect of the invention includes a method for contextual querying of co-occurrence data. The method includes selecting a next node in a connection network of nodes representing chemical or biological molecule names based on analysis of co-occurrence values.

Another aspect of the invention includes a method for query polling of co-occurrence data. The method includes determining an unknown target node in a connection network by generating Likelihood statistics for nodes prior to a position for the unknown target node and for nodes subsequent to the position for the unknown target node in the connection network.

Another aspect of the invention includes a method for creating automated inferences regarding the involvement of molecules in biological processes. The method includes generating automatically one or more inferences regarding relationships between chemical or biological molecules and biological processes.

The methods and system described herein may allow scientists and researchers to determine physico-chemical interaction knowledge from databases of co-occurrence data. The co-occurrence data includes co-occurrences between chemical or biological molecules or co-occurrences between chemical or biological molecules and biological processes.

The method and system may also be used to further facilitate a user's understanding of biological functions, such as cell functions, to design experiments more intelligently and to analyze experimental results more thoroughly. Specifically, the present invention may help drug discovery scientists select better targets for pharmaceutical intervention in the hope of curing diseases.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 3 is block diagram visually illustrating the method of FIGS. 2A and 2B;

FIG. 4 is a flow diagram illustrating a method for checking automatically created inferences;

FIG. 5 is a flow diagram illustrating a method for calculating a Likelihood statistic for co-occurrences;

DETAILED DESCRIPTION OF PREFERRED EMBODIMENTS

Exemplary Data Storage System

Figure 1:
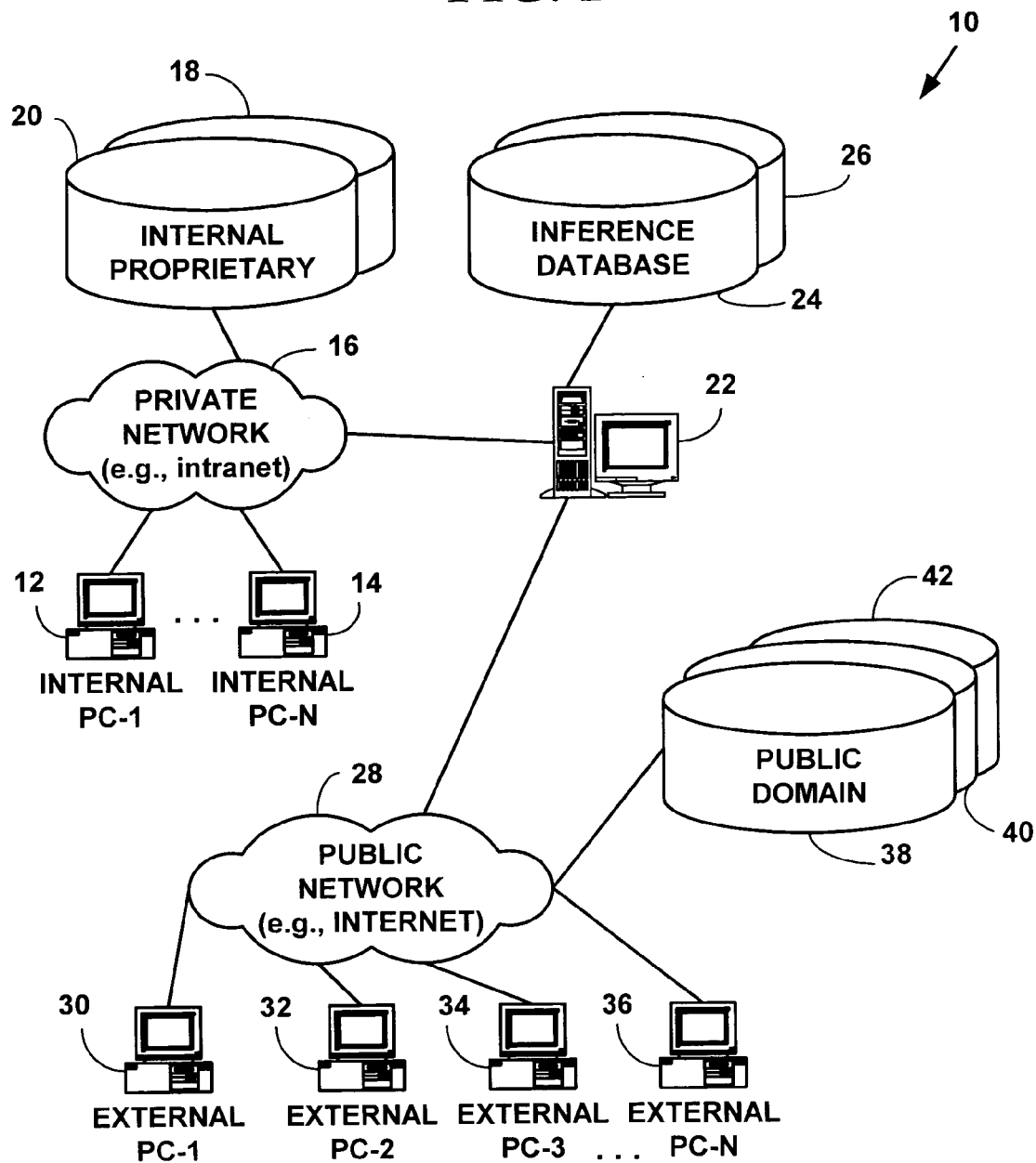
FIG. 1 illustrates an exemplary experimental data storage system for storing experimental data.

FIG. 1 illustrates an exemplary experimental data storage system 10 for one embodiment of the present invention. The data storage system 10 includes one or more internal user computers 12, 14, (only two of which are illustrated) for inputting, retrieving and analyzing experimental data on a private local area network ("LAN") 16 (e.g., an intranet). The LAN 16 is connected to one or more internal proprietary databases 18, 20 (only two of which are illustrated) used to store private proprietary experimental information that is not available to the public.

The LAN 16 is connected to an publicly accessible database server 22 that is connected to one or more internal inference databases 24, 26 (only two of which are illustrated) comprising a publicly available part of a data store for inference information. The publicly accessible database server 22 is connected to a public network 28 (e.g., the Internet). One or more external user computers, 30, 32, 34, 36 (only four of which are illustrated) are connected to the public network 28, to plural public domain databases 38, 40, 42 (only three of which are illustrated) and one or more databases 24, 26 including experimental data and other related experimental information available to the public. However, more, fewer or other equivalent data store components can also be used and the present invention is not limited to the data storage system 10 components illustrated in FIG. 1.

In one specific exemplary embodiment of the present invention, data storage system 10 includes the following specific components. However, the present invention is not limited to these specific components and other similar or equivalent components may also be used. The one or more internal user computers, 12, 14, and the one or more external user computers, 30, 32, 34, 36, are conventional personal computers that include a display application that provide a Graphical User Interface ("GUI") application. The GUI application is used to lead a scientist or lab technician through input, retrieval and analysis of experimental data and supports custom viewing capabilities. The GUI application also supports data exported into standard desktop tools such as spreadsheets, graphics packages, and word processors.

The internal user computers 12, 14, connect to the one or more private proprietary databases 18, 20, the publicly accessible database server 22 and the one or more or more public databases 24, 26 over the LAN 16. In one embodiment of the present invention, the LAN 16 is a 100 Mega-bit ("Mbit") per second or faster Ethernet, LAN. However, other types of LANs could also be used (e.g., optical or coaxial cable networks). In addition, the present invention is not limited to these specific components and other similar components may also be used.

In one specific embodiment of the present invention, one or more protocols from the Internet Suite of protocols are used so LAN 16 comprises a private intranet. Such a private intranet can communicate with other public or private networks using protocols from the Internet Suite. As is known in the art, the Internet Suite of protocols includes such protocols as the Internet Protocol ("IP"), Transmission Control Protocol ("TCP"), User Datagram Protocol ("UDP"), Hypertext Transfer Protocol ("HTTP"), Hypertext Markup Language ("HTML"), eXtensible Markup Language ("XML") and others.

The one or more private proprietary databases 18, 20, and the one or more publicly available databases 24, 26 are multi-user, multi-view databases that store experimental data. The databases 18, 20, 24, 26 use relational database tools and structures. The data stored within the one or more internal proprietary databases 18, 20 is not available to the public. Databases 24, 26, are made available to the public through publicly accessable database server 22 using selected security features (e.g., login, password, encryption, firewall, etc.).

The one or more external user computers, 30, 32, 34, 36, are connected to the public network 28 and to plural public domain databases 38, 40, 42. The plural public domain databases 38, 40, 42 include experimental data and other information in the public domain and are also multi-user, multi-view databases. The plural public domain databases 38, 40, 42, include such well known public databases such as those provided by Medline, GenBank, SwissProt, described below and other known public databases.

An operating environment for components of the data storage system 10 for preferred embodiments of the present invention include a processing system with one or more high speed Central Processing Unit(s) ("CPU") or other processor(s) and a memory system. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU executed," or "processor executed."

It will be appreciated that acts and symbolically represented operations or instructions include the manipulation of electrical signals by the CPU. An electrical system represents data bits which cause a resulting transformation or reduction of the electrical signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or may be distributed among multiple interconnected cooperating processing systems that may be local or remote to the processing system.

Creating Inferences Automatically

Figure 2A:
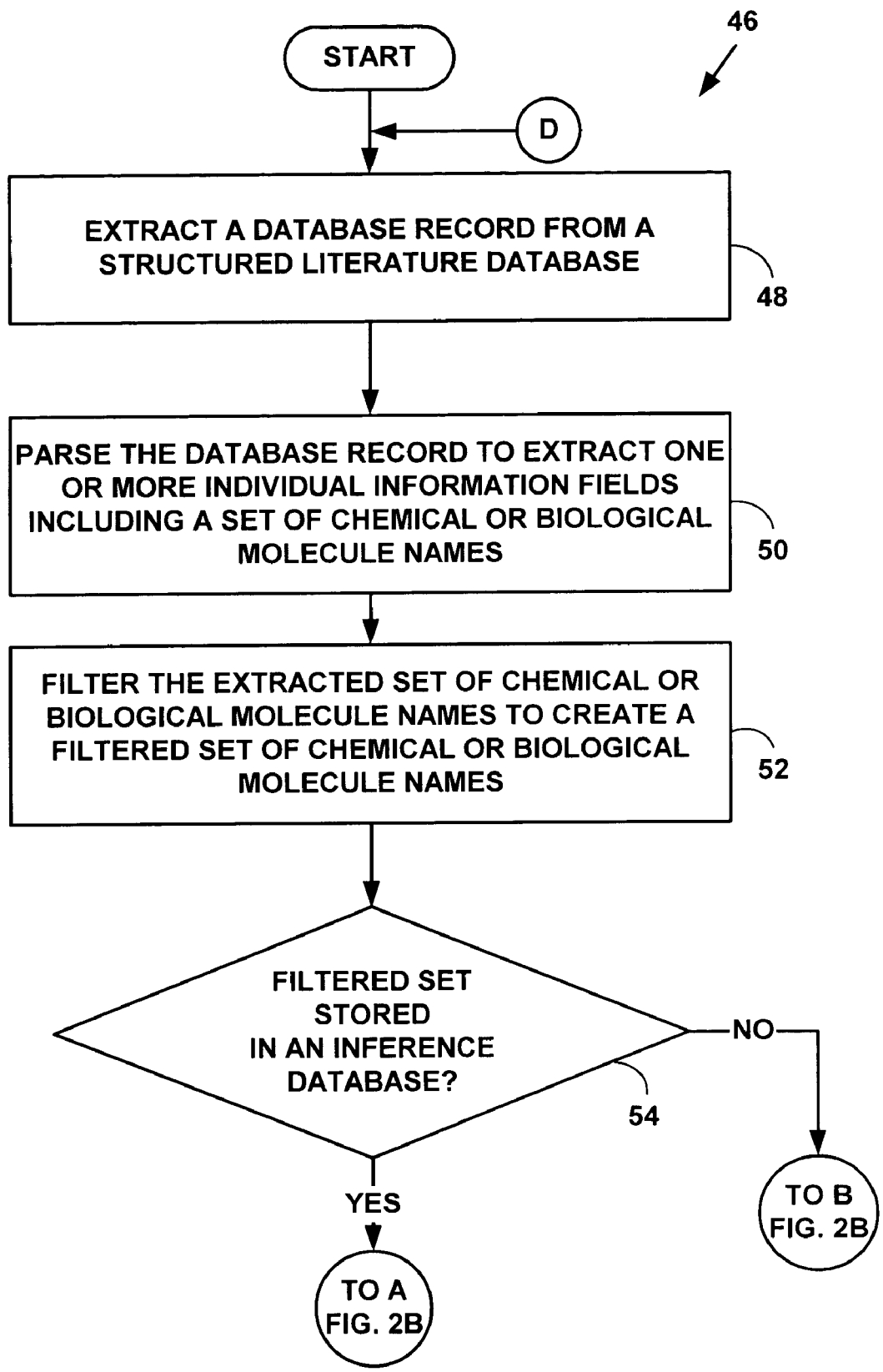
FIGS. 2A and 2B are a flow diagram illustrating a method for creating automated inferences.
Figure 2B:
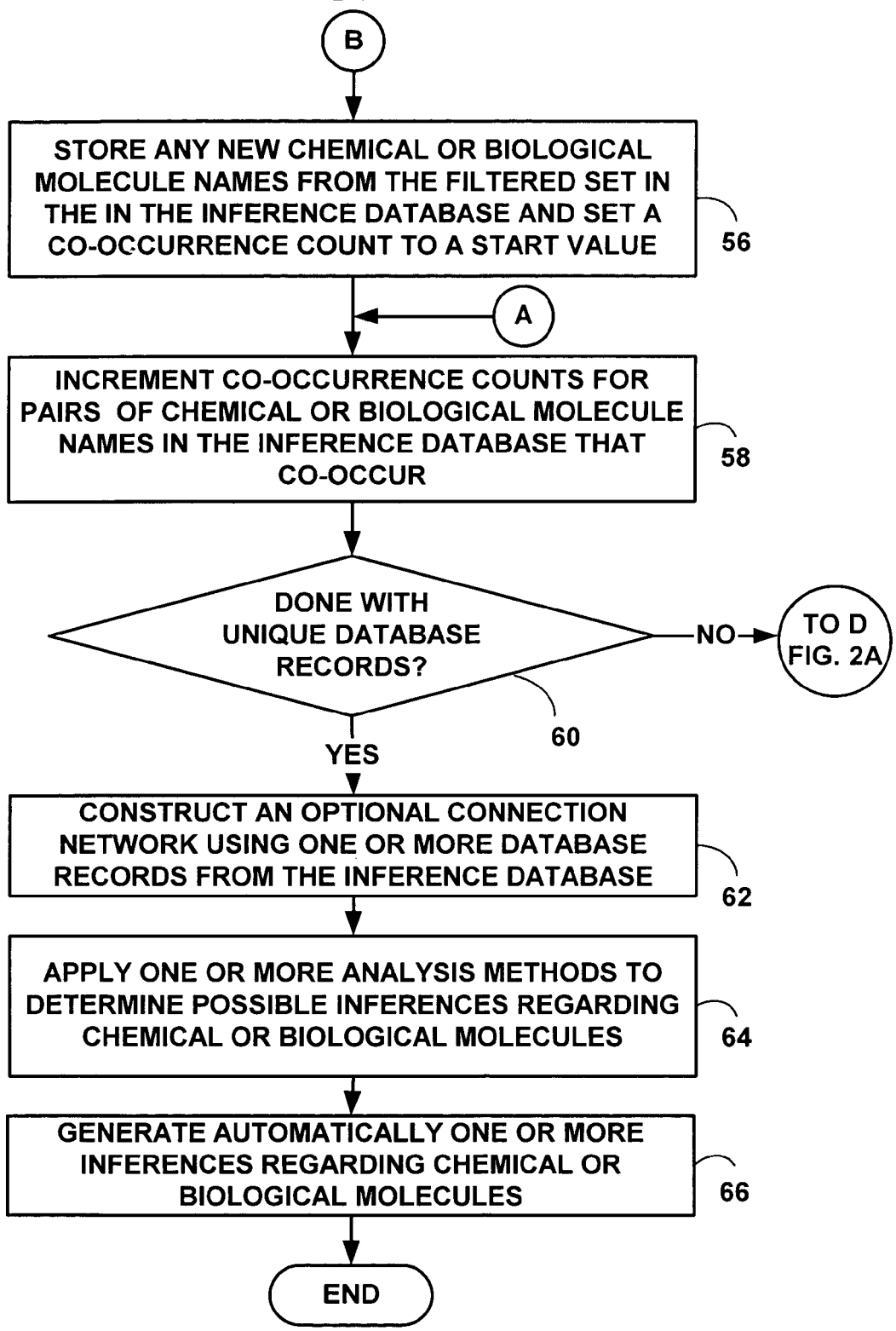

FIGS. 2A and 2B are a flow diagram illustrating a Method 46 for creating inferences automatically. In FIG. 2A at Step 48, a database record is extracted from a structured literature database. At Step 50, the database record is parsed to extract one or more individual information fields including a set (e.g., two or more) of chemical or biological molecule names. The chemical names include, for example, organic and inorganic chemical names for natural or synthetic chemical compounds or chemical molecules. The biological molecule names include, for example, natural (e.g. DNA, RNA, proteins, amino acids, etc.) or synthetic (e.g., bio-engineered) biological compounds or biological molecules. As used herein, "names" may include either textual names, chemical formulae, or other identifiers (e.g., GenBank accession numbers or CAS numbers). Hereinafter these chemical and biological molecule names are referred to as "chemical or biological molecule names" for simplicity.

At Step 52, the extracted set of chemical or biological names is filtered to create a filtered set of chemical or biological molecule names. At Step 54 a test is conducted to determine whether any chemical or biological molecule names in the filtered set have been stored in the inference database. If any of the chemical or biological molecule names in the filtered set have not been stored in an inference database, at Step 56 any new chemical or biological molecule names from the filtered set are stored in the inference database. Co-occurrence counts for each newly stored pair of chemical or biological molecule names in the set is initialized to a start value (e.g., one).

If a co-occurring pair of chemical or biological molecule names has already been stored in the inference database, in FIG. 2B at Step 58, a co-occurrence count for that pair of chemical or biological molecule names is incremented in the interference database. As is known in the art, a "co-occurrence" is a simultaneous occurrence of two (or more) terms (i.e., words, phrases, etc.) in a single document or database record. In one embodiment of the present invention, co-occurrence counts are incremented for every pair of chemical or biological molecules that co-occur. In another embodiment of the present invention, co-occurrence counts are incremented only for selected ones of chemical or biological molecules that co-occur based on a pre-determined set of criteria. Thus, Step 58 may include multiple iterations to increment co-occurrence counts for co-occurrences.

At Step 60 a loop is entered to repeat steps 48, 50, 52 for unique database records in the structured literature database. When the unique database records in the structured literature database have been processed, the loop entered at Step 60 terminates. At Step 62 an optional connection network is constructed using one or more database records from the inference database including co-occurrence counts. Preferred embodiments of the present invention may be used without executing Step 62. In such embodiments, Step 64 is executed directly on one or more database records from the inference database. The connection network is inherent in the inference database records.

At Step 64, one or more analysis methods are applied to the connection network or directly to one or more database records from the inference database to determine possible inferences regarding chemical or biological molecules. The possible inferences include inferences that particular physico-chemical interactions regarding chemical or biological molecules are known by experts to occur or thought by experts to occur. As is known in the art, "physico-chemical interactions" are physical contacts and/or chemical reactions between two or more molecules, leading to, or contributing to a biologically significant result. At Step 66, one or more inferences regarding chemical or biological molecule interaction knowledge are automatically (i.e., without further input) generated using results from the one or more analysis methods.

Method 46 is repeated frequently to update the inference database with new information as it appears in indexed scientific literature databases. This continually adds to the body of knowledge available in the inference database.

Method 46 is illustrated with one exemplary embodiment of the present invention used with biological information. However, present invention is not limited to such an exemplary embodiment and other or equivalent embodiments can also be used with Method 46. In addition Method 46 can be used with other than biological information, or with biological information in order to infer expert knowledge regarding relationships other than physico-chemical interactions regarding chemical or biological molecules.

In such an embodiment in FIG. 2A at Step 48, a database record is extracted from a structured literature database. What biologists have collectively determined regarding physico-chemical interactions regarding molecules in cells is collectively known as "knowledge," and is published in the open scientific literature. This knowledge is, therefore available for automated manipulation by computers. Although many scientific publications are now available in computer-readable (e.g., electronic) form, their textual content is generally not structured in such a way as to facilitate such automated extraction of information from that text (i.e., the computer-readable content is in "flat text" form.).

However, numerous indexing services exist to create databases of basic information regarding scientific publications (such as titles, authors, abstracts, keywords, 15 works cited, etc.). Examples include the National Library of Medicine's "*Medline*" and its Web interface, "*PubMed*" Biosis' "*Biological Abstracts*", the Institute for Scientific Information's "*Science Citation Index*" and others. Since these database records are structured they can be used for automated 20 analysis.

Additionally, several such indexes include information about the scientific articles they index (so-called "meta-data"). These meta-data, generally assigned by domain-knowledgeable human indexers, constitute an additional resource for automated analysis above and beyond the actual text of a scientific article. An example of such meta-data is an exemplary indexed database record (e.g, from Medline) illustrated in Table 1. However, the present invention is not limited to the meta-data illustrated in Table 1 and other or equivalent meta-data can also be used.

TABLE 1

| | |
|---|---|
| UI - | 98232076 |
| AU - | Rose L |
| AU - | Busa WB |
| TI - | Crosstalk between the phosphatidylinositol cycle and MAP kinase Signaling pathways in Xenopus mesoderm induction. |
| LA - | Eng |
| MH - | Animal |
| MH - | Biological Markers |
| MH - | Ca(2+)-Calmodulin Dependent Protein Kinase/*physiology |
| MH - | DNA-Binding Proteins/biosynthesis/genetics |
| MH - | Embryo, Nonmammalian/physiology |
| MH - | Embryonic Induction/*physiology |
| MH - | Fibroblast Growth Factor, Basic/*pharmacology |
| MH - | Gene Expression Regulation, Developmental/drug effects |
| MH - | Mesoderm/drug effects/*physiology |
| MH - | Microinjections |
| MH - | Phosphatidylinositols/*physiology |
| MH - | Receptors, Serotonin/drug effects/genetics |
| MH - | Recombinant Fusion Proteins/physiology |
| MH - | Serotonin/pharmacology |
| MH - | Signal Transduction/drug effects/*physiology |
| MH - | Transcription Factors/biosynthesis/genetics |
| MH - | Xenopus laevis/*embryology |
| RN - | EC 2.7.10.- (Ca(2+)-Calmodulin Dependent Protein Kinase) |
| RN - | 0 (serotonin 10 receptor) |
| RN - | 0 (Biological Markers) |
| RN - | 0 (Brachyury protein) |
| RN - | 0 (DNA-Binding Proteins) |
| RN - | 0 (Fibroblast Growth Factor, Basic) |
| RN - | 0 (Phosphatidylinositols) |
| RN - | 0 (Receptors, Serotonin) |
| RN - | 0 (Recombinant Fusion Proteins) |
| RN - | 0 (Transcription Factors) |
| RN - | 50-67-9 (Serotonin) |
| PT - | JOURNAL ARTICLE |
| DA - | 19980706 |
| DP - | 1998 Apr |
| IS - | 0012-1592 |
| TA - | Dev Growth Differ |
| PG - | 231-41 |
| SB - | M |
| CY - | JAPAN |
| IP - | 2 |
| VI - | 40 |
| JC - | E7Y |
| AA - | Author |
| EM - | 199809 |
| AB - | Recent studies have established a role for the phosphoinositide (PI) cycle in the early patterning of Xenopus mesoderm. In explants, stimulation of this pathway in the absence of growth factors does not induce mesoderm, but when accompanied by growth factor treatment, simultaneous PI cycle stimulation results in profound morphological and molecular changes in the mesoderm induced by the growth factor. This suggests the possibility that the PI cycle exerts its influence via crosstalk, by modulating some primary mesoderm-inducing pathway. Given recent identification of mitogen-activated protein kinase (MAPK) as an intracellular mediator of some mesoderm-inducing signals, the present study explores MAPK as a potential site of PI cycle-mediated crosstalk. We report that MAPK activity, like PI cycle activity, increases in intact embryos during mesoderm induction. Phosphoinositide cycle stimulation during treatment of explants with basic fibroblast growth factor (bFGF) synergistically increases late-phase MAPK activity and potentiates bFGF-induced expression of Xbra, a MAPK-dependent mesodermal marker. |
| AD - | Department of Biology, The Johns Hopkins University, Baltimore, MD 21218, U.S.A. |
| PMID - | 0009572365 |
| EDAT - | 1998/05/08 02:03 |
| MHDA - | 1998/05/08 02:03 |
| SO - | Dev Growth Differ 1998 Apr;40(2):231-41 |

In Table 1, each field of information is placed on a new line beginning with a two- to four-letter capitalized abbreviation followed by a hyphen. For example, the second and third fields in this record (beginning with "AU") identify the individual authors of the published article this record refers to. Such author names are extracted directly from the published article. In contrast, the information included in the record's RN fields indicates various chemical or biological molecules this article is concerned with. This meta-data is typically supplied by human indexers (e.g., in the case of Medline records, indexers at the National Library of Medicine, who study each article and assign RN values by selecting from a controlled vocabulary of chemical or biological molecule names).

At Step 50, the database record is parsed to extract one or more individual information fields including a set (two or more) chemical or biological molecule names. For example, using the information from Table 1, Step 50 would extract the multiple RN fields from the Medline record indicating various chemical or biological molecules used in the experiments described in the published article such as "RN EC 2.7.10.-(Ca(2+)-Calmodulin Dependent Protein Kinase)," etc.

At Step 52, the extracted set of chemical or biological names is filtered to create a filtered set of chemical or biological molecule names. In one embodiment of the present invention, chemical or biological molecule names in included the set of names extracted at Step 50 are filtered against a "stop-list" of trivial terms to be ignored. In the exemplary record from Table 1, the generic term "Biological Markers" is an exemplary trivial term to be ignored, as it represents a general concept rather than a specific chemical or biological molecule name.

At Step 52, the extracted set of chemical or biological names is filtered to create a filtered set of chemical or biological molecule names. At Step 54 a test is conducted to determine whether any chemical or biological molecule names in the filtered set have been stored in the inference database. If any of the chemical or biological molecule names in the filtered set have not been stored in an inference database, at Step 56 any new chemical or biological molecule names from the filtered set are stored in the inference database. Co-occurrence counts for each newly stored pair of chemical or biological molecule names in the set is initialized to a start value (e.g., one).

In one embodiment of the present invention, if, for an individual database record, two or more chemical or biological molecule names survive the filtering at Step 52, a co-occurrence of these names is recorded in an inference database record or in other computer-readable format.

If a co-occurring pair of chemical or biological molecule names has already been stored in the inference database, in FIG. 2B at Step 58, a co-occurrence count for that pair of chemical or biological molecule names is incremented in the interference database. Thus, Step 58 may include multiple iterations to increment co-occurrence counts for co-occurrences.

At Step 60 a loop is entered to repeat steps 48, 50, 52 for unique database records in the structured literature database. When the unique database records in the structured literature database have been processed, the loop entered at Step 60 terminates.

At Step 62, a connection network is optionally constructed using one or more database records from the inference database including co-occurrence counts. However, Step 64 can be executed directly without explicitly creating a connection network. A connection network is often created as to provide a visual aid to a researcher.

In one embodiment of the present invention, the connection network can be represented with an undirected-graph. As is known in the art, an undirected "graph" is a data structure comprising two or more nodes and one or more edges, which connect pairs of nodes. If any two nodes in a graph can be connected by a path along edges, the graph is said to be "connected."

In another embodiment of the present invention, the connection network is represented with a directed graph. As is known in the art, a "directed graph" is a graph whose edges have a direction. An edge or arc in a directed graph not only relates two nodes in a graph, but it also specifies a predecessor-successor relationship. A "directed path" through a directed graph is a sequence of nodes, $(n_1, n_2, \ldots n_k)$, such that there is a directed edge from $n_i$ to $n_{i+1}$ for all appropriate i.

It will be appreciated by those skilled in the art that the connection network or "graph" referred to here is inherent in the inference database. Constructing the connection network at Step 62 denotes storing the connection network in computer memory, on a display device, etc. as needed for automatic manipulation, automatic analysis, human interaction, etc. Constructing a connection network may also increase processing speed during subsequent analysis steps.

In one embodiment of the present invention, the connection network includes two or more nodes for one or more chemical or biological molecule names and one or more arcs connecting the two or more nodes. The one or more arcs represent co-occurrences regarding two chemical or biological molecules. An arc may have assigned to it any of several attributes that may facilitate subsequent analysis. In one specific embodiment of the present invention an arc has assigned to it a co-occurrence count (i.e., the number of times this co-occurrence was encountered in the analysis of the indexed scientific literature database). However the present invention is not limited to such a specific embodiment and other attributes can also be assigned to the arcs.

At Step 64, one or more analysis methods are applied to the connection network to determine possible inferences regarding chemical or biological molecules. Any of a wide variety of analysis methods, including statistical analysis are performed on the connection in order to distinguish those arcs which are highly likely to reflect physico-chemical interactions regarding chemical or biological molecules from those arcs which represent trivial associations.

At Step 66, one or more inferences regarding chemical or biological molecules are automatically (i.e., without further input) generated using the results of the analysis methods. These inferences may or may not later be reviewed by human experts and manually refined.

The present invention analyzes database indexes, such as Medline, which directly or indirectly indicate what chemical or biological molecules scientific articles are concerned with. If a scientific article reports evidence of the physico-chemical interaction of two or more chemical or biological molecules, then molecules will be referenced in the index's record for that article (e.g., in the case of Medline, each such molecule would be named in an RN field of the record for that article). Thus, a tabulation of co-occurrences of chemical or biological molecules within individual index records will include a more-or-less complete listing of known physico-chemical interactions regarding the chemical or biological molecules based on information in the indexed database.

Additionally, such a tabulation would include co-occurrences which do not reflect known physico-chemical interactions within cells, but rather reflect trivial relationships. For example, a scientific report might mention the protein, MAP kinase, and the simple salt, sodium chloride ("NaCl") in two distinct contexts without reporting a physico-chemical interaction between these molecules. Yet an indexer might nonetheless assign both of these chemical names to RN fields in this article's record. In this case, the co-occurrence of "MAP kinase" and "NaCl" within the Medline record would not reflect a physico-chemical interaction. Thus, the connection network of associations generated with Method 46 from a tabulation of co-occurrences will include known physico-chemical interactions that are biologically relevant as well as a (probably large) number of trivial associations between molecules that are biologically irrelevant.

In one embodiment of the present invention, the one or more inferences are stored in the inference database 24, 26.

In addition, subsequent analysis methods are applied to the inferences to reject trivial inferences. Such subsequent analysis methods may include, but are not limited to: (1) Assigning probabilities to arcs based simply on co-occurrence counts; (2) Assigning probabilities based on analysis of the temporal pattern of an association's co-occurrence count as a function of another variable (e.g., year of publication). For example, an association between two chemicals or biological molecules based on co-occurrences observed in ten articles published in 1996, with no additional co-occurrences observed in subsequent years, might well be a trivial association, whereas an association based on ten co-occurrences per year for the years 1996 through the current year might be judged likely to reflect a true physico-chemical interaction; (3) "Mutual information" analysis. For example a link between A and B may be most likely to reflect a known physico-chemical interaction if, in the indexed scientific literature database, both the presence of A's name in records has a probabilistic impact on the presence of B's name and the absence of A's name has a probabilistic impact on the absence of B's name; and (4) Citation analysis. As is known in the art, Citation analysis is a method for analyzing how related groups of technical documents are by analyzing the patterns of documents they reference or cite. It may be the case that articles in which a legitimate co-occurrence occurs cite each other much more frequently than do articles in which a trivial co-occurrence occurs.

FIG. 3 is a block diagram 68 visually illustrating selected steps of Method 46. In FIG. 2A at Step 48, an exemplary database record 70 (FIG. 3) is extracted from a structured literature database such as MedLine. At Step 50, the database record 70 is parsed to extract one or more individual information fields 72 (FIG. 3) including a set (two or more) chemical or biological molecule names. In this example, four fields beginning with RN from Box 70 are extracted as is illustrated by Box 72. At Step 52, the extracted set of chemical or biological names is filtered to create a filtered set of chemical or biological molecule names using a "stop-list" of chemical or biological molecule names. Box 74 of FIG. 3 illustrates one exemplary word, "Viral Proteins" to filter from the list of chemical or biological molecule names obtained from database record 70. At Step 54 a test is conducted to determine whether any of the chemical or biological molecule names from the filtered set of chemical and biological molecule names has been stored in an inference database 24, 26 (FIG. 1). If any of the chemical or biological molecule names from the filtered set of chemical and biological molecule names have not been stored in an inference database 24, 26, at Step 56 any new chemical and biological names are stored in the inference database as is illustrated with the exemplary database records in Box 76 of FIG. 3.

If a co-occurrence pair of chemical or biological molecules has already been stored in the inference database, in FIG. 2B at Step 58, co-occurrence counts for the chemical or biological molecule names are incremented in the interference database as is illustrated with Box 78 of FIG. 3. For example, Box 78 illustrates a co-occurrence count of 12 for Thrombin and the Herpes Simplex Virus Type 1 Protein UL9, a co-occurrence count of 5 for Thrombin and DNA, and a co-occurrence count of 44 for the Herpes Simplex Virus Type 1 Protein UL9 and DNA.

At Step 60 a loop is entered to repeat steps 48, 50, 52 for unique database records in the structured literature database. When the unique database records in the structured literature database have been processed, the loop entered at Step 60 terminates. In this example, loop 60 would have been executed at least 44 times for at least 44 unique records in the structured literature database as is indicated by the co-occurrence count of 44 in Box 78.

At Step 62 an optional connection network 80 is constructed using one or more database records from the inference database including co-occurrence counts. The exemplary connection network 80 includes three nodes and three arcs connecting the three nodes with assigned co-occurrence counts as illustrated. In this example, the nodes represent the chemical or biological molecule names (i.e., IDs 1-3) from Box 76. The arcs include co-occurrences counts illustrated in Box 78.

At Step 64, one or more analysis methods are applied to the connection network 80 or directly to database records in the inference database to determine any physico-chemical inferences between chemical or biological molecules. For example, when statistical methods are applied to the connection network 80, it is determined that there may be a strong inference between the Herpes Simplex Virus Type 1 Protein UL9 and DNA as is indicated by the highlighted co-occurrence count of 44' in connection network 80'.

At Step 66, one or more inferences 82 regarding chemical or biological molecules are automatically generated using the results from the one or more analysis methods. For example, an inference 84 is generated that concludes "The Herpes Simplex Virus Type 1 Protein UL9 interacts with DNA" based on the large co-occurrence count of 44.

Method 46 allows inferences, based on co-occurrences of chemical or biological names in indexed literature databases, regarding physico-chemical interactions between chemical or biological molecules to be automatically generated. Method 46 is described for co-occurrences. However, the Method 46 can also be used with other informational fields from indexed literature databases and with other attributes in the connection network and is not limited to determining inferences with co-occurrence counts.

Removing Trivial Inferences Automatically

FIG. 4 is a flow diagram illustrating a Method 86 for automatically checking generated inferences. At Step 88, connection network is created from an inference database including inference knowledge. The connection network includes two or more nodes representing one or more chemical or biological molecule names and one or more arcs connecting the two or more nodes. The one or more arcs represent co-occurrences between chemical or biological molecules. The inference database includes one or more inference database records including inference association information. The connection network can be explicitly created, or implicitly created from database records in the inference database as is discussed above. At Step 90, one or more analysis methods are applied to the connection network to determine any trivial inference associations. The one or more analysis methods can be applied to the connection network or to database records from the inference database as was discussed above. At Step 92, database records determined to include trivial inference associations are deleted automatically from the inference database, thereby improving the inference knowledge stored in the inference database.

Method 86 is illustrated with one specific exemplary embodiment of the present invention used with biological information. However, present invention is not limited to such an exemplary embodiment and other or equivalent embodiments can also be used with Method 86. In addition Method 86 can be used with other than biological information, or to infer other than physico-chemical interactions.

At Step 88, connection network 80 (FIG. 3) is created from an inference database 24,26 (FIG. 1) including inference knowledge. At Step 90, one or more analysis methods are applied to the connection network to determine any trivial inference associations. In one embodiment of the present invention, one or more of the subsequent analysis methods described above for Method 46 are applied at Step 90. However, other analysis methods could also be used and the present invention is not limited to the subsequent analysis methods described above. For example, the data in Box 78 reflects co-occurrences between Thrombin and DNA with a co-occurrence count of 5. However, this co-occurrence does not really reflect a physico-chemical interaction, but instead reflects a trivial relationship between these two biological molecule names. Such trivial inferences are removed from the inference database 24, 26. In the example of FIG. 3, the inference between nodes 1 and 3 is also judged to be trivial due to its low co-occurrence count.

At Step 92, database records determined to include trivial inferences with trivial co-occurrence counts are deleted automatically from the inference database, thereby improving the inference knowledge stored in the inference database. For example, the co-occurrence count of 5 in Box 78 for the trivial association between Thrombin (node 1) and DNA (node 3) would be removed, thereby improving the inference knowledge stored in the inference database. This deletion would also remove the arc with the co-occurrence count of 5 in the connection network 80 between nodes one and three if the connection network was stored in the inference database 24, 26.

A Co-occurrence Likelihood Statistic

It is also highly desirable to construct logical associations from the inferences created via co-occurrence analysis of indexed literature databases to represent a temporal sequence of physico-chemical interactions actually used by biological organisms (e.g., living cells) to regulate or to achieve a biological response. In molecular cell biology, such a temporal sequence of physico-chemical interactions is called a biological or cell "pathway."

The raw co-occurrence counts calculated by Method 46 do not initially attempt to distinguish and remove trivial co-occurrences from those that reflect known physico-chemical interactions. Trivial co-occurrences may have higher counts (i.e., frequencies) than do those reflecting actual physico-chemical interactions. As is known in the Information Retrieval arts, a wide variety of statistical methods have been employed to gauge the "strength" of co-occurrence data, including Chi and Chi Squared statistics, the Dice Coefficient, the Mutual Information statistic, and others. However, a more sophisticated statistical analysis of co-occurrence counts is typically required in order to distinguish and remove trivial co-occurrences.

FIG. 5 is a flow diagram illustrating a Method 96 for measuring a strength of co-occurrence data. At Step 98, two or more chemical or biological molecules names are extracted from a database record from an inference database. The inference database includes one or more inference database records created from a co-occurrence analysis of an indexed literature database. The two or more chemical or biological molecule names co-occur in one or more records of the indexed literature database. At Step 100, a Likelihood statistic $L_{AB}$ is determined for a co-occurrence between a first chemical or biological molecule name-A and a second chemical or biological molecule name-B extracted from the database record. At Step 102, the Likelihood statistic is applied to the co-occurrence to determine if the co-occurrence between the first chemical or biological molecule-A and the second chemical or biological molecule-B is a non-trivial co-occurrence reflecting actual physico-chemical interactions.

Method 96 is illustrated with one specific exemplary embodiment of the present invention used with biological information. However, present invention is not limited to such an exemplary embodiment and other or equivalent embodiments can also be used with Method 96. In addition Method 96 can be used with other than biological information.

In such an embodiment at Step 98, two or more chemical or biological molecules' names are extracted from a database record from an inference database 24, 26. For example, Thrombin and DNA are extracted from the exemplary database record 78 (FIG. 3). At Step 100, a Likelihood statistic $L_{AB}$ is determined for a co-occurrence reflecting physico-chemical interactions between a first chemical or biological molecule name-A and a second chemical or biological molecule name-B extracted from the database record as is illustrated in Equation 1. However, other or equivalent Likelihood statistics can also be used and the present invention is not limited to the Likelihood statistic illustrated in Equation 1.

$$L_{AB}=P(A|B)*P(\neg A|\neg B)*P(B|A)*P(\neg B|\neg A), \quad (1)$$

In Equation 1, A and B are two chemical or biological molecule names which co-occur in one or more database records.

In Equation 1, $P(A|B) \equiv$ the probability of A given B as is illustrated in Equation 2.

$$P(A|B)=c(AB)/c(B) \quad (2)$$

As is illustrated in Equation 2, $c(AB) \equiv$ a number of records in which A and B co-occur, and $c(B) \equiv$ a number of records in which B occurs either with or without A. In addition, the $P(B|A) \equiv$ the probability of B given A in Equation 1 includes $c(BA)/c(A)$ where $c(BA) \equiv$ a number of records in which B and A co-occur, and $c(A) \equiv$ a number of records in which A occurs either with or without B.

In Equation 1, $P(\neg A|\neg B)$ a probability of not A given not B as is illustrated in Equation 3.

$$P(\neg A|\neg B)=(N-(c(A)+c(B)-c(AB)))/(N-c(B)) \quad (3)$$

In Equation 3, $N \equiv$ a total number of records including co-occurrences of any chemical names, $c(AB) \equiv$ a number of records in which A and B co-occur, $c(A) \equiv$ a number of records in which A occurs either with or without B, and $c(B) \equiv$ a number of records in which B occurs either with or without A. $P(\neg B|\neg A)$ is determined in a similar manner as is illustrated in Equation 4.

$$P(\neg B|\neg A)=(N-(c(B)+c(A)-c(BA)))/(N-c(A)) \quad (4)$$

At Step 102, the Likelihood statistic $L_{AB}$ is applied to determine if the co-occurrence between the first chemical or biological molecule-A and the second chemical or biological molecule-B is a non-trivial co-occurrence reflecting actual physico-chemical interactions.

An example of the application of Method 96, consider three chemical or biological molecule names (X, Y, and Z) (e.g., X=Thrombin, Y=Herpes Simplex Virus Type 1 Protein UL9, and Z=laboratory reagent) occurring in the connection network 82 (FIG. 3) produced by Methods 46 or 96 and extracted at Step 98. Chemical or biological molecules X and Y participate in a crucially important physico-chemical interaction, so that X is seldom mentioned in the literature without reference to Y, and vice versa. Also assume (to simplify the illustration) that neither X nor Y is known to interact with any other chemical or biological molecules.

Thus, at Step 100 using Equation 1, P(X|Y) (Equation 2) will approach its maximum possible value of 1.0 (i.e., it is virtually certain that X will appear in any record in which Y appears), as will P(Y|X). Similarly, both P(¬X|¬Y) and P(¬Y|¬X) (Equation 3) will approach a maximum possible value of 1.0 (i.e., a record which does not mention one of these molecules is extremely likely to not mention the other). As a consequence, $L_{XY}$ (Equation 1) will take a value approaching 1.0.

In contrast, chemical Z is for example, a laboratory reagent essential to the study of the entire class of molecules of which X is a member. P(Z|X) will thus likely approach 1.0 (a record containing X is highly likely to contain Z, as well, since Z is widely employed in the study of X), whereas P(X|Z) is somewhat lower (i.e., the probability that a record mentioning Z will also mention X is less than 1) because the laboratory reagent Z is also employed in the study of some molecules other than X. P(¬X|¬Z) would be expected to be high (approaching 1.0), whereas P(¬Z|¬X) would be intermediate.

As a consequence, $L_{XZ}$ (Equation 1) would be expected to be significantly smaller number than $L_{XY}$, thus enabling a discrimination between biologically irrelevant and relevant (respectively) co-occurrences at Step 102. That is, a fractional value (e.g., a decimal fractional value such as 0.1, 0.2, etc. See Table 2 below) determined from Equation 1 is used to determine between trivial and non-trivial co-occurrences reflecting actual physico-chemical interactions between chemical or biological molecules. In this example, a value near zero indicates a trivial co-occurrence and a value near one indicates a non-trivial co-occurrence.

The Likelihood statistic $L_{AB}$ of Equation 1 may be a more suitable metric than the raw co-occurrence counts described above for analyzing the relationships in a co-occurrence connection network produced by Methods 46 and 86. In order to support the application of the Likelihood statistic, Methods 46 and 86 can be expanded to include tallying and storing co-occurrence counts (e.g., tallying records for c(AB) in Equations 2 and 3, above). If the Likelihood statistic $L_{AB}$ is used, Methods 46 and 86 are expanded to tally individual occurrence counts (c(A) and c(B)) and the total number of records analyzed (N in Equation 3) for use in determining the Likelihood statistic of Equation 1.

Contextual Querying

One use for the inference database including co-occurrences is to attempt to extract from it a true biological pathway (i.e., a particular sequence of physico-chemical interactions that regulate some cellular process). This task may be viewed as a special instance of the general class of problems known as connection network (or graph) traversal problems, the most familiar of which is the "Traveling Salesman Problem" ("TSP"). As is known in the art, in the TSP nodes of a network represent cities, the edges connecting those nodes are travel routes (e.g., roads or flights), each edge has a weight (e.g., distance between the cities it connects). The task is to visit each city once and only once while traveling the shortest distance possible.

In one embodiment of the present invention, nodes in the connection network represent chemical or biological molecules encountered in a co-occurrence analysis of the cell-biological literature, edges represent co-occurrences and may be weighted, for example, by Likelihood statistics (Equation 1). The task is to visit all the nodes (and only those nodes) that represent molecules known to be involved in pathway "X". The nodes are visited in the same order as their sequential physico-chemical interactions in pathway "X", using no information other than that included in the co-occurrence connection network itself.

A simplistic approach to accomplish this task would be to begin with any single node (molecule) A in the connection network, where A is asserted to be one component of the desired biological pathway (and thus serves here as a "seed"), and assume that the next node in the pathway is that adjacent node in the overall connection network (B, C, D, etc.) whose shared edge with A has the highest Likelihood statistic (or other metric, such as Chi, Chi Squared, Dice Coefficient, Mutual Information statistic, etc.). In practice, this approach often does not produce satisfactory results. For example, the chemical or biological molecule represented by a node may occur in two or more unique biological pathways, in which the simplistic approach is likely to yield a single "pathway" that is a combination or generalization of two or more genuine biological pathways. Similarly, if two or more of A's edges may have identical (or nearly identical) Likelihood statistics, a simplistic method is not able to resolve the ambiguity this presents.

Figure 6:
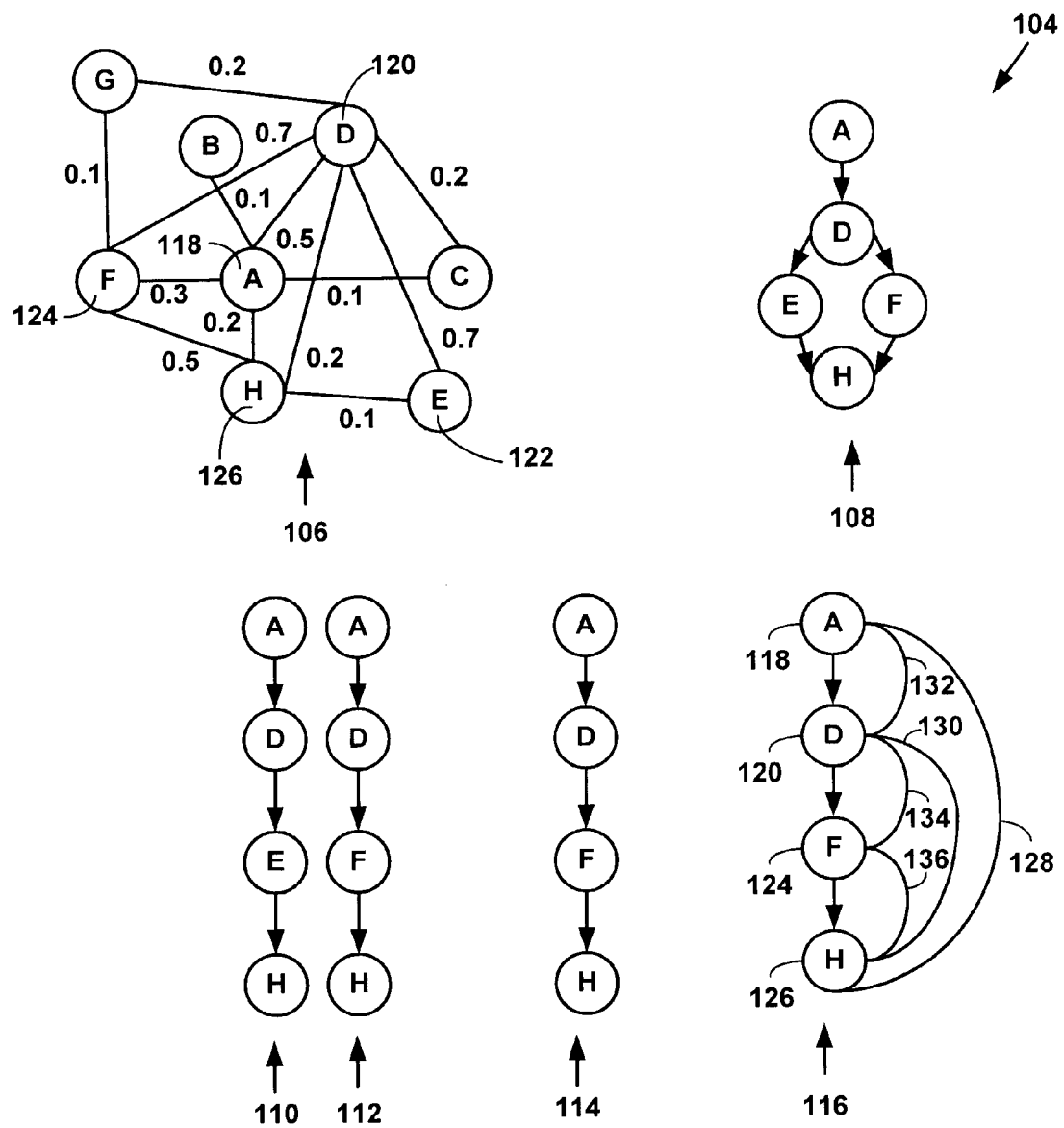
FIG. 6 is a block diagram illustrating exemplary extracted pathways used for contextual querying.

FIG. 6 is a block diagram illustrating exemplary extracted pathways 104 including exemplary pathways, 106, 108, 110, 112, 114 and 116, used for illustrating contextual querying. The co-occurrence connection network 108 can be interrogated in numerous ways to attempt to construct biological pathways from co-occurrence information. A naive method in pathway 108 starts with a "seed," in this case node A, and assumes that the next element in the pathway is a node sharing the most highly weighted edge with node A, in this example, node D with a Likelihood statistic weight of 0.5. In next pathway step, however, two nodes E and F share equally or nearly equally weighted co-occurrence edges (i.e., 0.7) with node D. See Table 2 below. It is unclear whether nodes E and F represent two distinct branches of a biological pathway 108, or whether only one of the two edges is legitimate as is illustrated by biological pathways, 110, 112. Contextual querying allows simultaneously considering co-occurrences with more than one prior node and provides unambiguous identification of a next node in a biological pathway (e.g., pathway 114).

Figure 7:
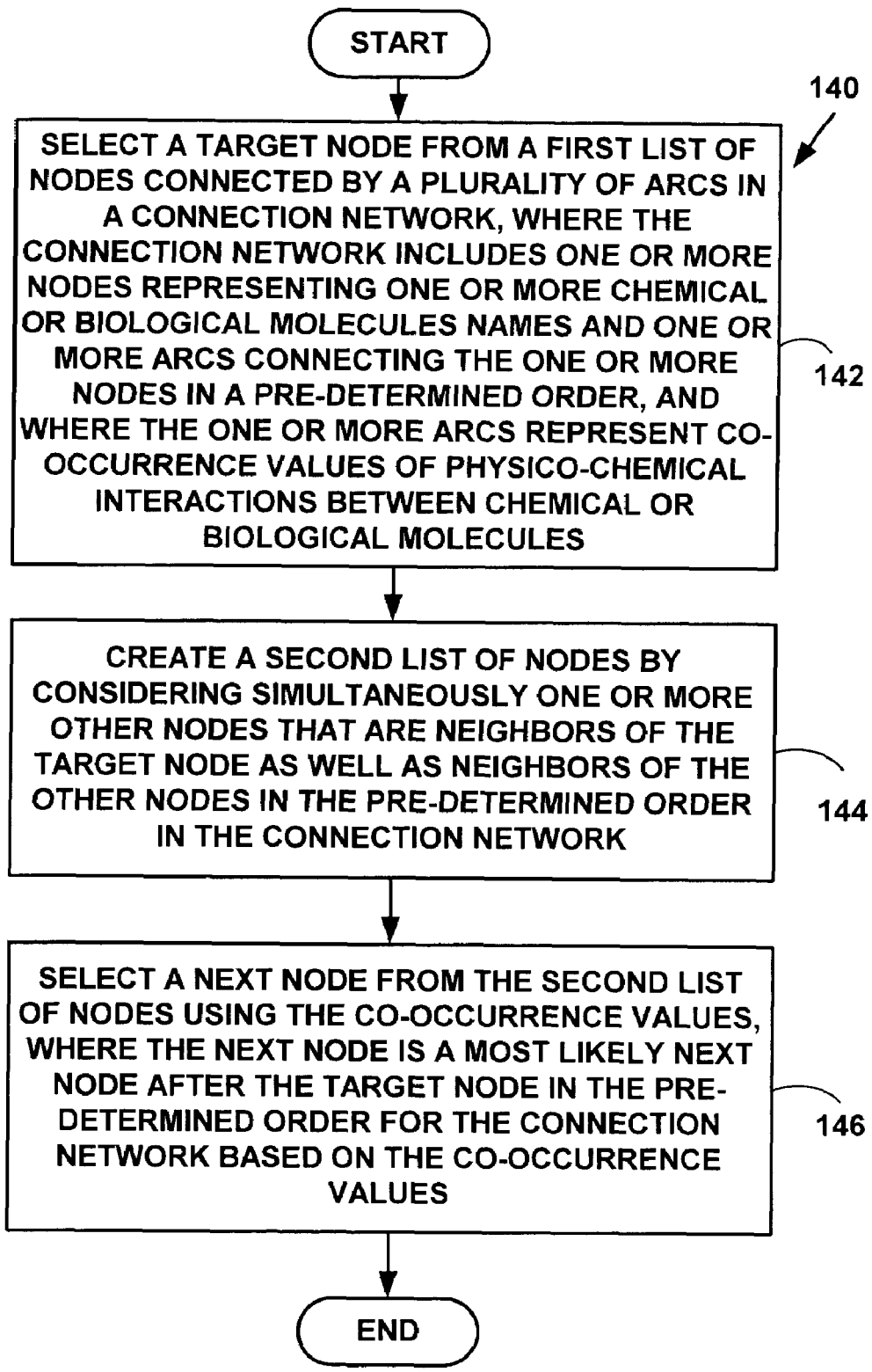
FIG. 7 is a flow diagram illustrating a method for contextual querying of co-occurrence data.

FIG. 7 is a flow diagram illustrating a Method 140 for contextual querying of co-occurrence data. At Step 142, a target node is selected from a first list of nodes connected by one or more arcs in a connection network. The connection network includes one or more nodes representing one or more chemical or biological molecules names and one or more arcs connecting the one or more nodes in a pre-determined order. The one or more arcs represent co-occurrence values of physico-chemical interactions between chemical or biological molecules. At Step 144, a second list of nodes is created by considering simultaneously one or more other nodes that are neighbors of the target node as well as neighbors of the other nodes prior to the target node in the connection network. At Step 146, a next node is selected from the second list of nodes using the co-occurrence values. The next node is a most likely next node after the target node in the pre-determined order for the connection network based on the co-occurrence values.

Method 140 is illustrated with one specific exemplary embodiment of the present invention used with biological information. However, present invention is not limited to such an exemplary embodiment and other or equivalent embodiments can also be used with Method 140. In addition Method 140 can be used with other than biological information.

In one embodiment of the present invention, contextual querying of Method 140 is used to solve the network traversal problem described above for biological pathways, employing heuristics that take advantage of how cell biological research is typically conducted and reported. In the course of biologists' discovery and analysis of a biological pathway (e.g., a cell pathway) it is seldom the case that the molecular interactions involved are reported in precisely the same temporal order as they occur in the pathway itself.

For example, returning to FIG. 6, the pathway 116 for nodes "A→D→F→H" 118, 120, 124, 126, might first have been hinted at in the biological literature by the observation that the activation of node A 118 elicits the activation of node H 126, and this published observation gives rise to a co-occurrence of molecule names A and H in an indexed scientific literature database, as indicated by arc 128. Other researchers might subsequently observe that the activation of node D 120 also results in the activation of node H 126, resulting in arc 130. Finally, subsequent reports might establish that the activation of node H 126 by node D 120 involves a physico-chemical interaction between nodes A 118 and node D 120, giving rise to arc 132, followed by an interaction between node D 120 and node F, giving rise to arc 134 which observations are then followed by research demonstrating the physico-chemical interaction of node F 122 and node H 126, giving rise to arc 136.

As a consequence of this temporal history of discovery, node F 124 will co-occur in the literature (within the context of the pathway under discussion) not only with node H 126 and D 120 (the only molecules it physically interacts with it in the biological pathway under discussion), but also with node A 118. Thus, given the "seed" A→D via arc 132 in connection network 116, the most likely next component of this biological pathway would be that neighbor of node D 120 (in the co-occurrence connection network 106) that likewise shares an edge with node A 118, where both these edges have relatively high weighted co-occurrence statistic (e.g., 0.7). Node F 124 is such a node.

Returning to FIG. 7 at Step 146, a next node is selected from the second list of nodes using the co-occurrence values. Referring to the co-occurrence connection network 106 shown in FIG. 6, the next node best meeting these criteria is node F 124 (instead of node E 122), which is thus the next likely component in the pathway that begins with nodes A→D.

If the co-occurrence connection network 106 of FIG. 6 is implemented as a relational database in one preferred embodiment of the invention, contextual querying with Method 140 may (but need not necessarily) be implemented using sub-queries in a structured query language ("SQL") or any other query language used to query relational databases.

Table 2 illustrates entries from an exemplary inference relational database based on the connection network 106 from FIG. 6.

TABLE 2

CHEM_PAIRS FOR CONNETION NETWORK 106

| CHEM 1 | CHEM 2 | LIKELIHOOD VALUE |
|---|---|---|
| A | B | 0.1 |
| A | C | 0.1 |
| A | D | 0.5 |

TABLE 2-continued

CHEM_PAIRS FOR CONNETION NETWORK 106

| CHEM 1 | CHEM 2 | LIKELIHOOD VALUE |
|---|---|---|
| A | F | 0.3 |
| A | H | 0.2 |
| C | D | 0.2 |
| D | E | 0.7 |
| D | F | 0.7 |
| D | H | 0.2 |
| D | G | 0.2 |
| E | H | 0.1 |
| F | G | 0.1 |
| F | H | 0.5 |

For the exemplary relational database illustrated in Table 2, a suitable query (incorporating a subquery) for determining the next node in the pathway "A→D→?" is illustrated in Table 3.

TABLE 3

SELECT Chem_2, Likelihood FROM Chem_Pairs
WHERE Chem_1 = 'D' AND Chem_2 IN
(SELECT Chem_2 FROMChem_Pairs
WHERE Chem_1 = 'A')

The query illustrated in Table 3 will return the connection network neighbors of node D 120 that are also neighbors of node A 118 using Method 140. This query will return node F 124 at Step 146 instead of node E 122. In one embodiment of the present invention, software issuing this SQL query selects from the result list (i.e., second list) that node with the highest Likelihood statistic value (i.e., node F).

In the example illustrated in Table 3, the context of the query is composed of nodes A 118 and D 120. However, larger contexts (i.e., composed of more than two components) are also typically used. Table 4 illustrates queries that return all of the neighbors of node F 124 that are also neighbors of nodes D 120 and A 118.

TABLE 4

SELECT Chem_2, Likelihood FROM Chem_Pairs
WHERE Chem_1 = 'F' AND Chem_2 IN
(SELECT Chem_2 FROM Chem_Pairs
WHERE Chem_1 ='D' AND Chem_2 IN
(SELECT Chem_2 FROM Chem_Pairs
WHERE Chem 1 = 'A'))

The query in Table 4 employs as its context components nodes A 118, D 120, and F 124 via nested subqueries, and returns all the neighbors of nodes F 124 that are also neighbors of nodes D 120 and A 118. This query will return node H 126.

Query Polling

The contextual queries illustrated with Method 140 may be viewed as "extrapolation queries." Such extrapolation queries answer the question: given two or more sequential nodes, what is the next node in the sequence? An extension of contextual querying supports "interpolation queries" using query polling. Such interpolation queries answer the question: given one or more upstream nodes and one or more downstream nodes in a pathway what is the identity of an unknown target node situated between the upstream and downstream nodes?

For example, for the pathway "A→D→?→F," an identity of the node being sought is indicated by the question mark "?". In one embodiment of the present invention, two contextual queries are used to arrive at the answer; one employing the context "A→D→?," for known upstream nodes and the other employing the context "?→F," for known downstream nodes.

Figure 8:
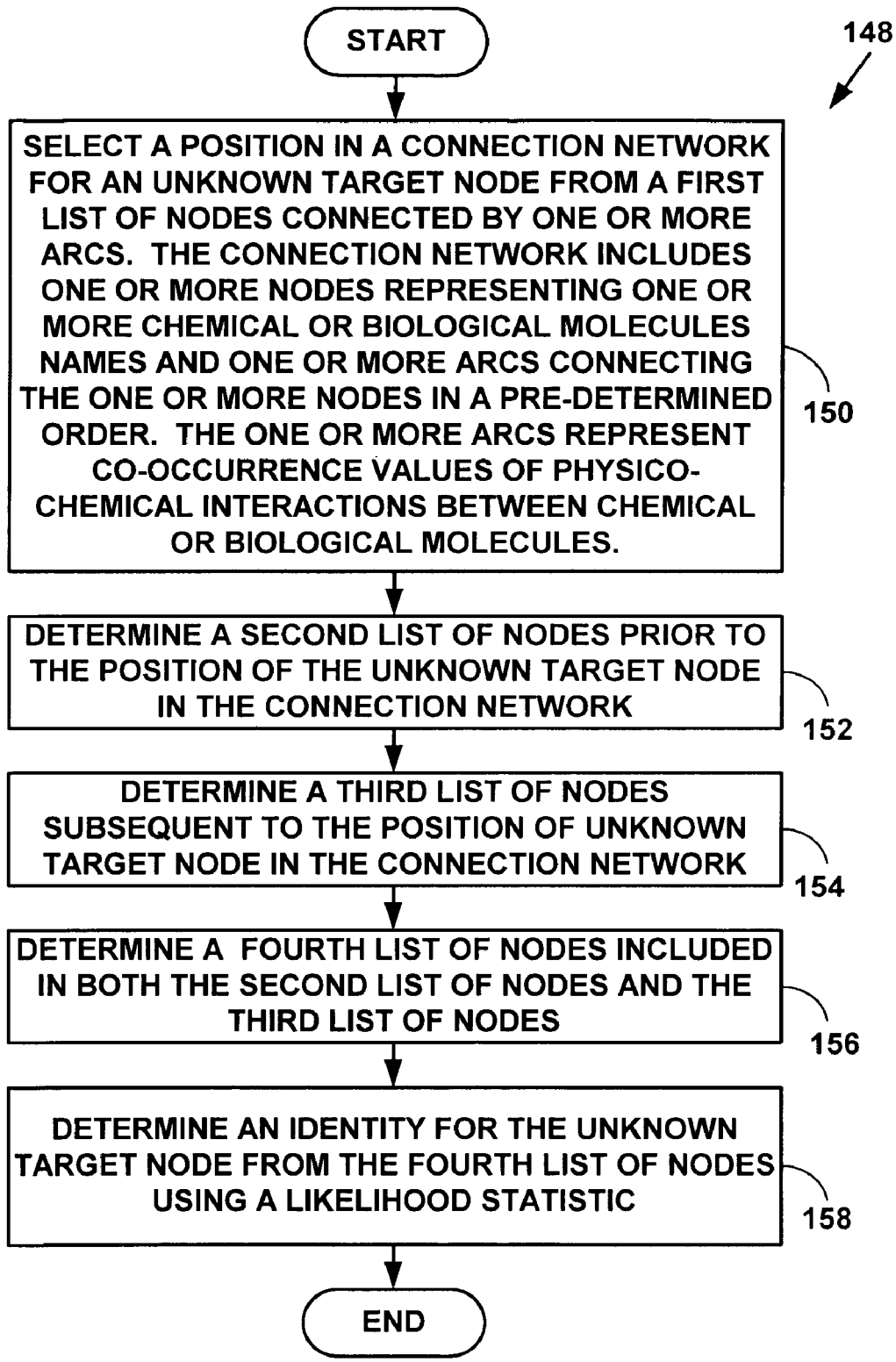
FIG. 8 is a flow diagram illustrating a method for query polling of co-occurrence data.

FIG. 8 is a flow diagram illustrating a Method 148 for query polling of co-occurrence data. At Step 150, a position in a connection network is selected for unknown target node from a first list of nodes connected by one or more arcs. The connection network includes one or more nodes representing one or more chemical or biological molecules names and one or more arcs connecting the one or more nodes in a pre-determined order. The one or more arcs represent co-occurrence values of chemical or biological molecule names in a structured database (e.g., an indexed scientific literature database). At Step 152, a second list of nodes prior to the position of the unknown target node in the connection network is determined. At Step 154, a third list of nodes subsequent to the position of unknown target node in the connection network is determined. At Step 156, a fourth list of nodes is determined included in both the second list of nodes and the third list of nodes. At Step 158, an identity for the unknown target node is determined by selecting a node using the fourth list of nodes and a Likelihood statistic. The Likelihood statistic includes a co-occurrence value reflecting physico-chemical interactions between a first chemical or biological molecule-A and a second chemical or biological molecule-B.

Method 148 is illustrated with one specific exemplary embodiment of the present invention used with biological information. However, present invention is not limited to such an exemplary embodiment and other or equivalent embodiments can also be used with Method 148. In addition Method 148 can be used with other than biological information.

In such an embodiment at Step 150, a position in a connection network is selected for unknown target node from a first list of nodes connected by a plurality of arcs. For example, in the exemplary the pathway A→D→?→F from the connection network 106 where the position of the node being sought is indicated by the question mark "?".

At Step 152, a second list of nodes prior to the position of the unknown target node in the connection network is determined. At Step 154, a third list of nodes subsequent to the position of unknown target node in the connection network is determined. In one exemplary embodiment of the present invention, two exemplary SQL queries to determine the second and third lists are executed at Steps 152 and 154. The exemplary SQL queries are illustrated in Table 5.

TABLE 5

SELECT Chem_2, Likelihood FROM Chem_Pairs
WHERE Chem_1 = '0' AND Chem_2 IN
(SELECT Chem_2 FROM Chem_Pairs
WHERE Chem_1 = 'A')
And
SELECT Chem_2, Likelihood FROM Chem_Pairs
WHERE Chem 1 = 'F' AND Chem_2 IN
(SELECT Chem_2 FROM Chem_Pairs The second list of nodes determined at Step 152 includes the set of nodes {C, E, F, H, G}. The third list of nodes determined at Step 154 includes the set of nodes {A, D, H, G}. Results from the SQL queries in Table 5 performed on connection network 106 (FIG. 6) with Steps 152 and 154 are illustrated in Table 6.

TABLE 6

| Result Set for Query 3: A → D → ? | | Result Set for Query 4: ? → F | |
|---|---|---|---|
| Chem_2 | Likelihood | Chem_2 | Likelihood |
| C | 0.2 | A | 0.3 |
| E | 0.7 | D | 0.7 |
| F | 0.7 | H | 0.5 |
| H | 0.2 | G | 0.3 |
| G | 0.2 | | |

At Step 156, a fourth list of nodes is determined included in both the second list of nodes and the third list of nodes. In this example, the forth list of nodes includes the set {(H, 0.2, G, 0.2 (e.g., from the second set), (H, 0.5, G, 0.3 (e.g., from the third set)}. In this example, a total of seven nodes are returned at Steps 152 and 154. At Step 156, only two nodes are returned G and H, which are common to both result sets.

At Step 158, an identity for the unknown target node is determined by selecting a node from the fourth list of nodes using a Likelihood statistic. In one embodiment of the present invention, an identity for the unknown target node is determined with a highest "simultaneous" Likelihood statistic value (Equation 1) e.g., (fourth list of nodes) over all result sets (e.g., the second and third list of nodes).

In one preferred embodiment of the present invention, an identity for the unknown target node is determined by selecting nodes in the fourth set and multiplying each node's Likelihood statistic determined from the second list of nodes by its Likelihood statistic value determined in the third set of nodes, and choosing as a single node with a largest Likelihood statistic product value.

In this example, the fourth list of node includes the set {(H, 0.2, G, 0.2,), (H, 0.5, G, 0.3)}. The simultaneous Likelihood statistic value for node H is H 0.2 (second set)×H 0.5 (third set), or 0.2×0.5=0.1. The simultaneous Likelihood statistic value for node G is G 0.2 (second set)×G 0.3 (third set), or 0.2×0.3=0.06. Thus, node H is selected for the unknown target node based on its larger simultaneous Likelihood statistic product value since the simultaneous Likelihood statistic product value for node H of 0.1 is greater than the simultaneous Likelihood statistic product value for node G of 0.06.

Other possible embodiments of the present invention involve selecting only the largest Likelihood statistic value, and then potentially using a tie-breaking scheme for equal Likelihood statistic values, adding (rather than multiplying) the separate Likelihood statistic values, or using other mathematical manipulations on the Likelihood statistic values.

Query polling is thus a method for selecting a single best answer to select a node in a pathway from two or more result sets of nodes by considering a simultaneous Likelihood of each result across all result sets. In other embodiments of the present invention it may be preferable to have all of this processing performed within a single complex query (i.e., SQL or other query), rather than using multiple queries plus post-processing of the result sets.

Creating Biological Process Inferences

In Method 46 above, the meta-data tallied as to co-occurrence included meta-data concerning the names of chemical or biological molecules indexed in scientific literature records. However, the Medline database described above also contains other human indexer-assigned metadata, most notably terms derived from the Medical Subject Headings ("MESH") vocabulary identifying a biological process, biological response, or disease state (hereafter called "biological process(es)") that each indexed scientific article concerns (e.g., "apoptosis" or "signal transduction.", etc.).

Figure 9:
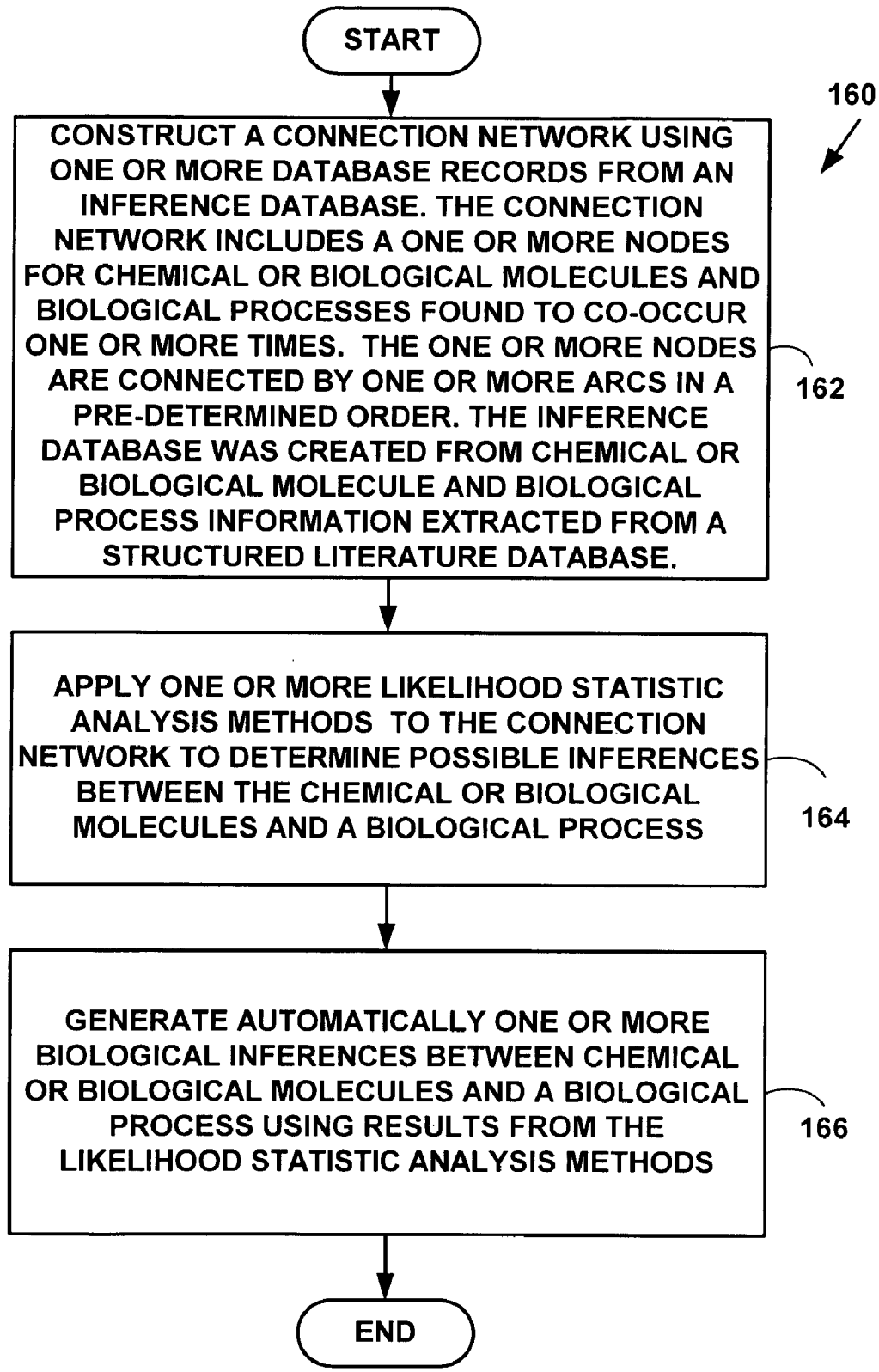
FIG. 9 is a flow diagram illustrating a method for creating automated biological inferences.

FIG. 9 is a flow diagram illustrating a Method 160 for creating automated biological inferences. At Step 162, a connection network is constructed using one or more database records from an inference database. The connection network includes a one or more nodes for chemical or biological molecules and biological processes found to co-occur one or more times. The one or more nodes are connected by one or more arcs in a pre-determined order. The inference database was created from chemical or biological molecule and biological process information extracted from a structured literature database. At Step 164, one or more Likelihood statistic analysis methods are applied to the connection network to determine possible inferences regarding functional relationships between the chemical or biological molecules and a biological process. At Step 166, one or more inferences are automatically generated regarding the chemical or biological molecules and a biological process using results from the Likelihood statistic analysis methods.

Method 160 is illustrated with one specific exemplary embodiment of the present invention used with biological information. However, present invention is not limited to such an exemplary embodiment and other or equivalent embodiments can also be used with Method 160.

At Step 162, a connection network is constructed using one or more database records (e.g., Table 2) from an inference database 24, 26. The connection network includes a one or more nodes for chemical or biological molecules and biological processes found to co-occur one or more times. The one or more nodes are connected by one or more arcs in a pre-determined order. The inference database 24, 26 was created from chemical or biological molecule and biological process information extracted from a structured literature database 38, 40, 42 (e.g., MedLine and others) with method 46 described above.

At Step 164, one or more Likelihood statistic analysis methods are applied to the connection network to determine possible inferences regarding functional relationships between the chemical or biological molecules and a biological process. In one embodiment of the present invention, the Likelihood statistic of Equation 1 is preferably applied. In another embodiment of the present invention other analysis methods such as Chi, Chi Square, Dice Coefficient, etc. may be employed to infer the likely relevance of each chemical or biological molecule/biological process co-occurrence. However, in such embodiments, the terms A and B in Equations 1, 2 and 3 (above) would represent, respectively, a chemical or biological molecule and a biological process (and not a two chemical or biological molecules) found to co-occur one or more times in the indexed scientific literature database such as Medline, etc.

At Step 166, one or more inferences are automatically generated regarding chemical or biological molecules and a biological process using results from the Likelihood statistic analysis methods. The inferences concern a collection of chemical or biological molecules logically associated with biological processes or, conversely, a collection of biological processes logically associated with a chemical or biological molecule. As discussed above, some of these associations will be trivial—that is, biologically irrelevant. For example, a common laboratory reagent such as "water" associated with a disease such as "cancer." Such trivial associations can be removed with Method 86 (FIG. 4) or method 96 (FIG. 5).

However, many inferences will be biologically relevant, indicative of the biological involvement of chemical or biological molecule(s) in biological process(es). For example, the association of the molecules "cyclic AMP", "calcium", and "inositol 1,4,5-trisphosphate" with the process "signal transduction", in which process the chemical or biological molecules are known to play important roles in cell biology.

The inferences generated with method 160 from co-occurrences of chemical or biological molecules and biological processes is useful in a number of ways. In one embodiment of the present invention, gene expression profiles may be analyzed, to classify them according to the biological process(es) they reflect, by querying the chemical or biological molecule/biological process co-occurrence inference database constructed by Method 46 for the one or more biological process(es) that co-occur(s) most frequently or, additionally or alternatively, with highest simultaneous Likelihood statistic(s), with the genes said gene expression profile reveals to be up-regulated or down-regulated under pre-determined experimental conditions.

In another embodiment of the present invention, cell-based High Content Screening data (e.g., HCS cell data) involving changes in activity, localization, concentration, etc. of multiple biological or chemical molecules (e.g., two protein kinases, one protease, and two second messengers) can be analyzed by this same means to determine the biological process(es) reflected by these changes. In yet another embodiment of the present invention, the converse question can be asked—given a biological process of interest (e.g., a cellular process of interest in the context of drug discovery), what are all of the biological or chemical molecules known to be involved in this process?

The present invention thus may constitute an automated means of answering common questions regarding the chemical or biological molecules related to particular biological processes (and vice versa) much more rapidly than the usual means of answering such questions, which commonly involves introspection, study, and manual literature searching by knowledgeable domain experts (e.g., molecular cell biologists).

The methods and system described herein can be used construct logical associations from the inferences created via co-occurrence analysis of indexed literature databases, to represent a temporal sequence (e.g., a cell pathway) of physico-chemical interactions actually used by living organisms (e.g., cells) to regulate or to achieve a biological response.

The present invention may also be used to further facilitate a user's understanding of biological functions, such as cell functions, to design experiments more intelligently and to analyze experimental results more thoroughly by automatically biological inferences with co-occurrences. Specifically, the present invention may help drug discovery scientists select better targets for pharmaceutical intervention in the hope of curing diseases. The method and system may also help facilitate the abstraction of knowledge from information for biological experimental data and provide new bioinformatic techniques.

In view of the wide variety of embodiments to which the principles of the present invention can be applied, it should be understood that the illustrated embodiments are exemplary only. The illustrated embodiments should not be taken as limiting the scope of the present invention.

For example, the steps of the flow diagrams may be taken in sequences other than those described, and more or fewer elements may be used in the block diagrams. While various elements of the preferred embodiments have been described as being implemented in software, in other embodiments in hardware or firmware implementations may alternatively be used, and vice-versa.

The claims should not be read as limited to the described order or elements unless stated to that effect. Therefore, all embodiments that come within the scope and spirit of the following claims and equivalents thereto are claimed as the invention.

I claim:

1. A method for creating automated biological inferences, the method comprising:

constructing a connection network using one or more database records from an inference database, wherein the connection network includes a plurality of nodes for chemical or biological molecules and biological processes found to co-occur one or more times, wherein the plurality of nodes are connected by a plurality of arcs in a pre-determined order, and wherein the inference database was created from chemical or biological molecule and biological process information extracted from a structured literature database;

applying Likelihood statistic analysis methods to the connection network to determine possible inferences between the chemical or biological molecules and biological processes; and generating automatically one or more biological inferences regarding relationships between chemical or biological molecules and biological processes using results from the Likelihood statistic analysis methods;

outputting the one or more biological inferences to a user;

wherein the step of applying Likelihood statistic analysis methods to the connection network includes applying a Likelihood statistic calculated by:

$$L_{AB}=P(A|B)*P(\neg A|\neg B)*P(B|A)*P(\neg B|\neg A)$$

wherein A and B are two chemical or biological molecule names which co-occur in one or more database records, wherein $P(A|B)$=(the probability of A given B), $P(B|A)$=(the probability of B given A), wherein $P(\neg A|\neg B)$=(the probability of not A given not B) and $P(\neg B|\neg A)$=(the probability of not B given not A).

2. The method of claim 1 wherein the chemical or biological molecules and biological processes co-occur in a cell.

3. The method of claim 1 wherein the plurality of arcs connecting the plurality of nodes in a pre-determined order includes a biological pathway.

4. The method of claim 1 wherein the step generating automatically one or more biological inferences includes generating a collection of a plurality of chemical or biological molecules logically associated with a plurality of biological processes, or a collection of a plurality of biological processes logically associated with a chemical or biological molecule.

5. The method of claim 1 wherein the step of generating automatically one or more biological inferences between chemical or biological molecules and a biological process using results from the Likelihood statistic analysis methods includes generating automatically one or more biological inferences between chemical or biological molecules and a biological process in a cell using results from the Likelihood statistic analysis methods.

6. The method of claim 1 further comprising a computer readable medium having stored therein instructions for causing a processor to execute the steps of the method.

* * * * *

UNITED STATES PATENT AND TRADEMARK OFFICE
CERTIFICATE OF CORRECTION

PATENT NO. : 7,356,416 B2
APPLICATION NO. : 09/768686
DATED : April 8, 2008
INVENTOR(S) : William B. Busa Page 1 of 7

It is certified that error appears in the above-identified patent and that said Letters Patent is hereby corrected as shown below:

Drawings
Sheet 3, replace Fig. 2B with the figure depicted below, wherein in step 56 "IN THE IN THE" has been changed to --IN THE--

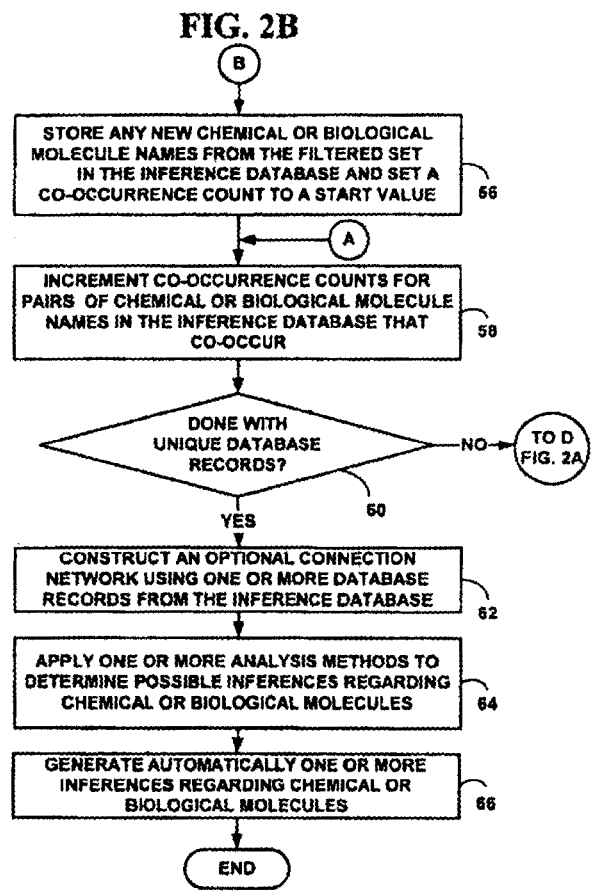

UNITED STATES PATENT AND TRADEMARK OFFICE
CERTIFICATE OF CORRECTION

PATENT NO.        : 7,356,416 B2
APPLICATION NO.   : 09/768686
DATED             : April 8, 2008
INVENTOR(S)       : William B. Busa It is certified that error appears in the above-identified patent and that said Letters Patent is hereby corrected as shown below:

Sheet 4, replace Fig. 3 with the figure depicted below, wherein in box 78, "4" has been changed to --5--

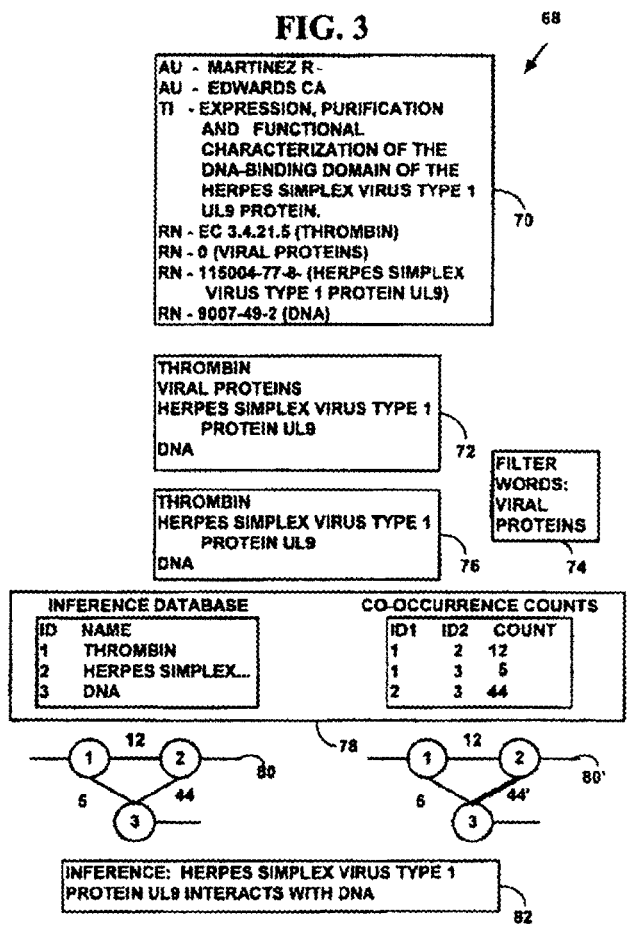

UNITED STATES PATENT AND TRADEMARK OFFICE
CERTIFICATE OF CORRECTION

PATENT NO.        : 7,356,416 B2                                    Page 3 of 7
APPLICATION NO. : 09/768686
DATED             : April 8, 2008
INVENTOR(S)       : William B. Busa It is certified that error appears in the above-identified patent and that said Letters Patent is hereby corrected as shown below:

Sheet 8, replace Fig. 7 with the figure depicted below, wherein in step 142 "MOLECULES NAMES" has been changed to --MOLECULE NAMES--

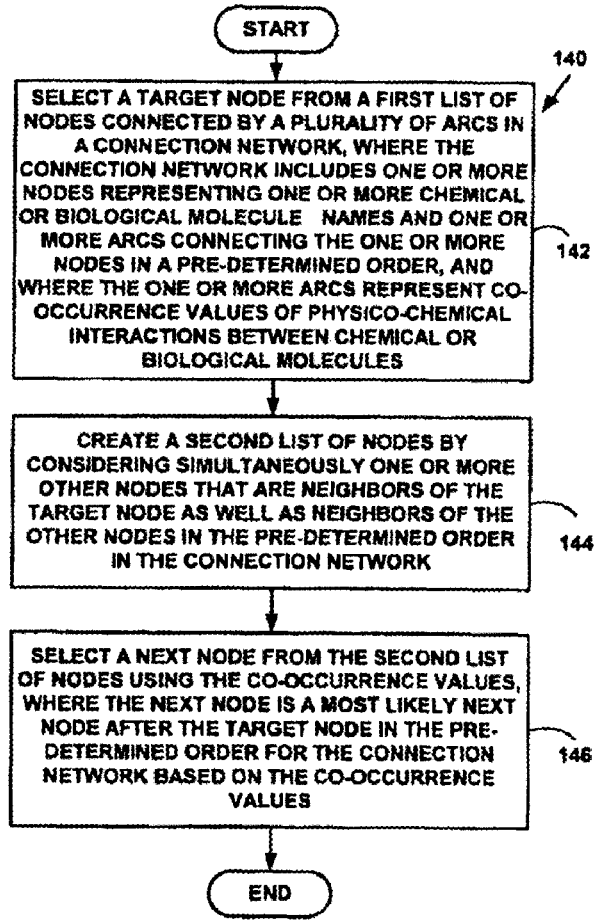

UNITED STATES PATENT AND TRADEMARK OFFICE
CERTIFICATE OF CORRECTION

| | | |
|---|---|---|
| PATENT NO. | : 7,356,416 B2 | Page 4 of 7 |
| APPLICATION NO. | : 09/768686 | |
| DATED | : April 8, 2008 | |
| INVENTOR(S) | : William B. Busa | |

It is certified that error appears in the above-identified patent and that said Letters Patent is hereby corrected as shown below:

Sheet 9, replace Fig. 8 with the figure depicted below, wherein in step 150 "MOLECULES NAMES" has been changed to --MOLECULE NAMES--

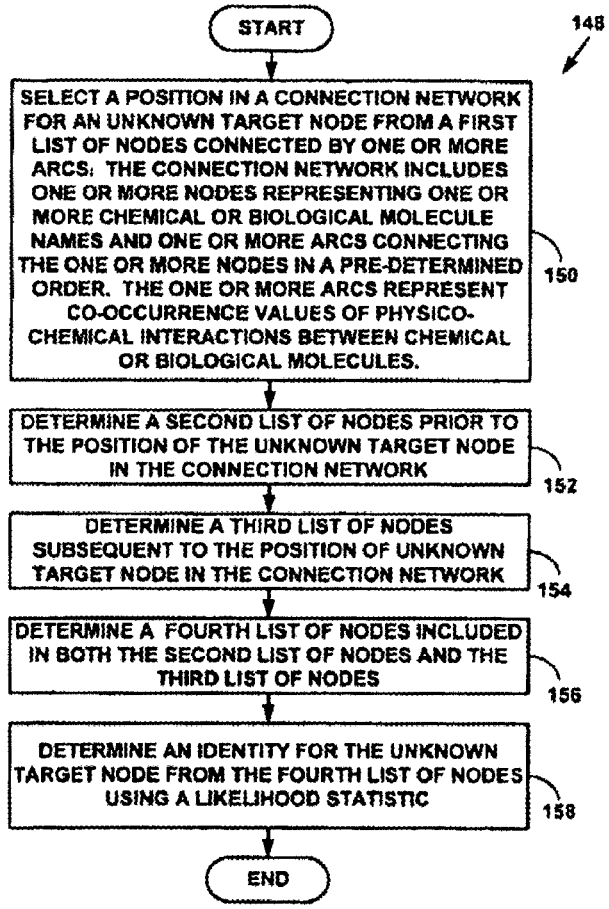

UNITED STATES PATENT AND TRADEMARK OFFICE
CERTIFICATE OF CORRECTION

| | | |
|---|---|---|
| PATENT NO. | : 7,356,416 B2 | |
| APPLICATION NO. | : 09/768686 | |
| DATED | : April 8, 2008 | |
| INVENTOR(S) | : William B. Busa | |

It is certified that error appears in the above-identified patent and that said Letters Patent is hereby corrected as shown below:

Column 3
Line 23, change ""Bioknowledge Library" This" to --"Bioknowledge Library." This--

Column 5
Lines 16-17, change "checking automatically" to --automatically checking--

Column 8
Line 57, change "20 analysis." to --analysis.--

Column 9
Table 1, in the twenty-fourth entry, change "0 (serotonin 10 receptor)" to --0 (serotonin 1C receptor)-- as depicted herein below.

RN -    0 (serotonin 1C receptor)

Column 9
Table 1, in the forty-seventh entry, change the multiple instances of "P1" to --PI-- as depicted herein below.

AB -    Recent studies have established a role for the phosphoinositide (PI) cycle in the early patterning of Xenopus mesoderm. In explants, stimulation of this pathway in the absence of growth factors does not induce mesoderm, but when accompanied by growth factor treatment, simultaneous PI cycle stimulation results in profound morphological and molecular changes in the mesoderm induced by the growth factor. This suggests the possibility that the PI cycle exerts its influence via crosstalk, by modulating some primary mesoderm-inducing pathway. Given recent identification of mitogen-activated protein kinase (MAPK) as an intracellular mediator of some mesoderm-inducing signals, the present study explores MAPK as a potential site of PI cycle-mediated crosstalk. We report that MAPK activity, like PI cycle activity, increases in intact embryos during mesoderm induction. Phosphoinositide cycle stimulation during treatment of explants with basic fibroblast growth factor (bFGF) synergistically increases late-phase MAPK activity and potentiates bFGF-induced expression of Xbra, a MAPK-dependent mesodermal marker.

Column 11
Line 10, change "in included the set" to --included in the set--
Line 51, change "as to" to --to--

UNITED STATES PATENT AND TRADEMARK OFFICE
CERTIFICATE OF CORRECTION

PATENT NO.       : 7,356,416 B2
APPLICATION NO.  : 09/768686
DATED            : April 8, 2008
INVENTOR(S)      : William B. Busa It is certified that error appears in the above-identified patent and that said Letters Patent is hereby corrected as shown below:

Column 14
Line 25, change "84" to --82--

Column 16
Line 42, change "$P(\neg A | \neg B)$ a" to --$P(\neg A | \neg B) \equiv$ a--
Line 64, change "network 82" to --network 80--

Column 18
Line 51, change "molecules names" to --molecule names--

Column 19
Line 26, change "Node F," to --Node F 124,--
Line 29, change "122" to --124--

Column 20
Replace Table 4 with the table depicted below, wherein "WHERE Chem 1 = 'A'" has been changed to --WHERE CHEM_1 = 'A'--

TABLE 4

```
SELECT Chem_2, Likelihood FROM Chem_Pairs
WHERE Chem_1 = 'F' AND Chem_2 IN
(SELECT Chem_2 FROM Chem_Pairs
WHERE Chem_1 = 'D' AND Chem_2 IN
(SELECT Chem_2 FROM Chem_Pairs
WHERE Chem_1 = 'A'))
```

Column 21
Line 14, change "molecules names" to --molecule names--

Replace Table 5 with the table depicted below, wherein: "WHERE Chem_1 = 'O' AND CHEM_2 IN" has been changed to --WHERE Chem_1 = 'D' AND Chem_2 IN-- and the second "(SELECT Chem_2 FROM Chem_Pairs" has been changed to --(SELECT Chem_2 FROM Chem_Pairs)--

TABLE 5

```
    SELECT Chem_2, Likelihood FROM Chem_Pairs
    WHERE Chem_1 = 'D' AND Chem_2 IN
    (SELECT Chem_2 FROM Chem_Pairs
    WHERE Chem_1 = 'A')
And
    SELECT Chem_2, Likelihood FROM Chem_Pairs
    WHERE Chem 1 = 'F' AND Chem_2 IN
    (SELECT Chem_2 FROM Chem_Pairs)
```

UNITED STATES PATENT AND TRADEMARK OFFICE
CERTIFICATE OF CORRECTION

PATENT NO. : 7,356,416 B2
APPLICATION NO. : 09/768686
DATED : April 8, 2008
INVENTOR(S) : William B. Busa It is certified that error appears in the above-identified patent and that said Letters Patent is hereby corrected as shown below:

Column 23
Line 6, change ""signal transduction."," to --"signal transduction,"--

Column 24
Line 50, change "construct" to --to construct--
Line 61, change "biological" to --checking biological--

Column 25
Line 10, change "embodiments in" to --embodiments--

Signed and Sealed this

Seventeenth Day of February, 2009

JOHN DOLL
*Acting Director of the United States Patent and Trademark Office*